US007208525B2

(12) United States Patent
Kohno et al.

(10) Patent No.: US 7,208,525 B2
(45) Date of Patent: Apr. 24, 2007

(54) DIAGNOSTIC AGENTS FOR PANCREATIC EXOCRINE FUNCTION

(75) Inventors: Tadashi Kohno, Tokyo (JP); Isaburo Hosoi, Tokyo (JP); Asuka Ito, Tokyo (JP); Junko Hirayama, Tokyo (JP); Kenji Maeda, Tokyo (JP)

(73) Assignee: Tokyo Gas Company Limited, Tokyo (JP)

( * ) Notice: Subject to any disclaimer, the term of this patent is extended or adjusted under 35 U.S.C. 154(b) by 132 days.

(21) Appl. No.: 10/482,571

(22) PCT Filed: Feb. 22, 2002

(86) PCT No.: PCT/JP02/01588

§ 371 (c)(1), (2), (4) Date: Dec. 24, 2003

(87) PCT Pub. No.: WO03/015832

PCT Pub. Date: Feb. 27, 2003

(65) Prior Publication Data

US 2005/0147557 A1 Jul. 7, 2005

(30) Foreign Application Priority Data

Aug. 10, 2001 (JP) ............................ 2001-243142

(51) Int. Cl.

| | |
|---|---|
| ***A61K 31/195*** | (2006.01) |
| ***C07K 5/06*** | (2006.01) |
| ***C07K 5/065*** | (2006.01) |
| ***C07K 5/062*** | (2006.01) |
| ***C07K 5/072*** | (2006.01) |

(52) U.S. Cl. ...................................................... 514/563

(58) Field of Classification Search ..................... None
See application file for complete search history.

(56) References Cited

FOREIGN PATENT DOCUMENTS

| | | | |
|---|---|---|---|
| CA | 2273549 | A1 * | 12/1999 |
| EP | 0 966 975 | A2 | 12/1999 |
| EP | 1 101 499 | A2 | 5/2001 |

OTHER PUBLICATIONS

B.J. Gour-Salin et al. Can. J. Chem. (1991) 69(8), pp. 1288-1297. STN/CAS Abstract only.*
A. Albeck and S. Kliper. Biochem. J. (2000) 346, pp. 71-76.*
"Pancreatic enzymes" by Tadashi Kohno et al., Japan J. Pharmacol., vol. 85, Sup. 1/The 74th Annual Meeting, Mar. 1, 2001, published by The Japanese Pharmacological Society, S22-3.
"Procedure for the Semisyntheses of Peptide Amides having a Glutamic or Aspartic Acid α-Amide at the C-terminal" by Henriksen, Dennis B. et al., Protein and Peptide Letters, 1998, vol. 5, No. 3, pp. 141-146.

* cited by examiner

*Primary Examiner*—Cecilia J. Tsang
*Assistant Examiner*—Andrew D. Kosar
(74) *Attorney, Agent, or Firm*—Finnegan, Henderson, Farabow, Garrett & Dunner LLP

(57) ABSTRACT

A diagnostic agent for pancreatic exocrine function comprising a dipeptide represented by the following formula (I):

$$X_1—R_1—Y_1 \quad (I)$$

or a pharmaceutically acceptable salt thereof,
wherein $X_1$ is a protecting group,
$R_1$ is a phenylalanine, glutamine, valine, tyrosine, methionine, serine or threonine residue, and
Y1 is a $^{13}$C-labeled alanine molecule optionally having a protecting group.

4 Claims, 19 Drawing Sheets

DIAGNOSTIC AGENTS FOR PANCREATIC EXOCRINE FUNCTION

This is a U.S. national phase application under 35 U.S.C. 371 of International Patent Application Ser. No. PCT/JP02/01588 filed Feb. 22, 2002, and claims the benefit of Japanese Patent Application No. 2001-243142 filed Aug. 10, 2001. The International Application was published in Japanese on Feb. 27, 2003 as WO 03/015832 A1 under PCT Article 21(2).

TECHNICAL FIELD

The present invention relates to diagnostic agents for pancreatic exocrine function and novel compounds.

BACKGROUND ART

"Pancreatic exocrine function tests" are useful for the diagnosis of pancreatic diseases such as chronic and acute pancreatitis and pancreatic cancer. It is also useful to assess the condition and the prognosis of patients and to manage the administration of medicine: The general descriptions are found in Arvanitakis and Cooke, Gastroenterology, 74:932 (1978); Niederau and Grendell, Gastroenterology, 88:1973 (1985); Goldberg, Bull. Mol. Biol. Med., 15:1 (1990); Lankisch, Int. J. Pancreatology, 14:9 (1993); Bank and Chow, Gastroenterologist, 2:224 (1994); and Steer et al., New Eng. J. Med., 332:1482 (1995).

The pancreatic exocrine function tests are roughly classified into intubation tests and tubeless tests. The intubation tests involve intubating a tube through the mouth to the duodenum to collect the duodenal juice. The secretin test is commonly used wherein secretin is intravenously administered to stimulate secretion of the pancreatic juice prior to the collection. This method is highly accurate since the amounts and components of the pancreatic juice are directly analyzed, and is regarded as the "gold standard" of pancreatic exocrine function test. However, this method can not be used repeatedly or used for screening purposes because of the very strong stress caused on the patients. It is only available at a relatively small number of clinical settings since the physician must be highly skilled. Further, since this method requires fluoroscopic tube placement during the collection of the duodenal juice, there is the problem of X ray exposure.

On the other hand, tubeless tests are easy to perform for estimating the pancreatic exocrine function without requiring intubation and the excreted amount of compounds produced by pancreatic exocrine enzymes or the excreted amount of the pancreatic exocrine enzymes per se is measured. At present, the following four methods are mainly used:

1. PFD test wherein a synthetic substrate BT-PABA (N-benzoyl-L-tyrosyl-p-aminobenzoic acid) for chymotrypsin secreted from the pancreas is orally administered and the amount of PABA (p-aminobenzoic acid), a product degradated by chymotrypsin, excreted into the urine is measured;
2. PLT test wherein a synthetic substrate FDL (fluorescein dilaurate) for cholesterol ester hydrolase, esterase, secreted from the pancreas is orally administered and the amount of the degradation product fluorescein excreted into the urine or the concentration thereof in the blood is measured;
3. Fecal chymotrypsin test wherein chymotrypsin in the feces is quantitatively determined; and 4. Fecal elastase test wherein elastase in the feces is quantitatively determined.

However, the sensitivity of any of these tests is too low to detect slight decreases in pancreatic exocrine function.

In order to solve this problem, many convenient pancreatic exocrine function tests have been searched for; $^{13}$C-breath tests have also been applied wherein a $^{13}$C-labeled compound is administered and an increase of the concentration of $^{13}CO_2$ in the exhalation is measured. Examples of such $^{13}$C-breath tests are illustrated below:

1. $^{13}$C-breath test wherein a $^{13}$C-labeled lipid or mixed triglyceride, which is a substrate for lipase, is administered [Chen et al., J. Nuclear Med., 15:1125 (1974); Watkins et al., J. Lab. Clin. Med., 90:422 (1977); Ghoos et al., Digestion, 22:239 (1981); John, S G., Gastroenterology, 83:44 (1982); Watkins et al., Gastroenterology, 82:911 (1982); Benini et al., Digestion, 29:91 (1984); Jones et al., J. Lab. Clin. Med., 105:647 (1985); Knoblach et al., Monatsschr Kinderheilkd, 136:26 (1988); Vantrappen et al., Gastroenterology, 96:1126 (1989); Murphy et al., Arch. Disease in Childhood, 65:574 (1990); Kato et al., Am. J. Gastroenterol., 88:64 (1993); McClean et al., Arch. Disease in Childhood, 69:366 (1993); Jakobs et al., Eur. J. Pediatr., 156:S78 (1997); and Kalivianakis et al., Eur. J. Clin. Invest., 27:434 (1997)];
2. $^{13}$C-breath test wherein a $^{13}$C-labeled cholesterol ester, which is a substrate for cholesterol esterase, a lipase, is administered [Mundlos, et al., Pediatric Res., 22:257 (1987); Cole et al., Gastroenterology, 93:1372 (1987); and Mundlos et al., Gut, 31:1324 (1990)];
3. $^{13}$C-breath test wherein a $^{13}$C-labeled starch, which is a substrate for an amylase, is administered [Hiele et al., Gastroenterology, 96:503 (1989); Dewit et al., Pediatric Res., 32:45 (1992); and Z. Gastroenterol., 35:187 (1997)]; and
4. $^{13}$C-breath test wherein a $^{13}$C-enriched egg protein, which is a protein having a $^{13}$C-concentration increased up to 1.4 atm % from the natural abundance of 1.1 atm % by feeding a chicken with $^{13}$C-leucine, and which is a substrate for a protease, is administered [Y. Ghoos, $^{13}CO_2$-Breath Tests at the laboratory "Digestion-Absorption", University Hospital Gasthuisberg, Leuven, Belgium (1996)].

However, all these methods are of low sensitivity and time-consuming. Therefore, these methods have not been established in clinical fields.

As a highly sensitive pancreatic exocrine function test method that resolves the problems of the above-described convenient methods and $^{13}$C-breath tests, puts less burden on subjects, and gives accurate results immediately, a breath test using 13C-labeld peptides ($^{13}$C-peptide breath test) has been proposed (Japanese Unexamined Patent Publication No. 2000-053697).

It is an object of the present invention to provide diagnostic agents for pancreatic exocrine function whose dose required for one test can be reduced without decreasing the degree of increase of $^{13}$C concentration in exhaled $CO_2$ ($\Delta^{13}C$(‰)) in the $^{13}$C-peptide breath test which is a highly sensitive pancreatic exocrine function test that puts only small burden on subjects and which gives accurate results immediately.

It is another object of the present invention to provide novel compounds which may be used in pancreatic exocrine function tests using $^{13}$C-breath tests.

DISCLOSURE OF THE INVENTION

In order to reduce the dose of a diagnostic agent required for one test, it is necessary to select a dipeptide that gives a high degree of increase of $^{13}C$ concentration in exhaled $CO_2$ ($\Delta^{13}C$(‰)) in $^{13}C$-breath tests.

The present inventors have carried out $^{13}C$-breath tests in which $^{13}C$-dipeptides having the structure of protecting group-amino acid-($^{13}C$-Ala) are administered to rats equimolarly, and compared the resultant $\Delta^{13}C$(‰) values. As a result, the inventors have found that certain kinds of $^{13}C$-dipeptides show higher $\Delta^{13}C$(‰) values than Bz-Ala-($^{13}C$-Ala) which gave the highest $\Delta^{13}C$(‰) value in Examples of Japanese Unexamined Patent Publication No. 2000-053697. Thus, the present invention has been achieved.

The present invention provides a diagnostic agent for pancreatic exocrine function comprising a dipeptide represented by the following formula (I) or a pharmaceutically acceptable salt thereof.

$$X_1—R_1—Y_1 \quad (I)$$

wherein $X_1$ is a protecting group, $R_1$ is a phenylalanine, glutamine, valine, tyrosine, methionine, serine or threonine residue, and $Y_1$ is a $^{13}C$-labeled alanine molecule optionally having a protecting group.

The present invention also provides a dipeptide represented by the following formula (II) or a pharmaceutically acceptable salt thereof.

$$X_2—R_2—Y_2 \quad (II)$$

wherein $X_2$ is a protecting group, $R_2$ is a phenylalanine, glutamine, valine, tyrosine, methionine, serine or threonine residue, and $Y_2$ is a $^{13}C$-labeled alanine molecule optionally having a protecting group.

The dipeptide represented by the formula (II) or salts thereof may be used as an active ingredient in a diagnostic agent for pancreatic exocrine function. Although tests are possible in which the concentration of a $^{13}C$-labeled compound is measured in serum, urine or stool after the administration of the diagnostic agent, breath tests are desirable in which an increase in $^{13}C$ concentration is measured in the exhaled $CO_2$ after the administration.

Hereinbelow, the present invention will be described in detail.

Peptides are herein indicated in such a manner that the N-termini are on the left and the C-termini are on the right.

Amino acid residues are shown herein in three-letter abbreviations. They may be L-isomers, D-isomers or DL-isomers.

The term "dipeptide" used herein refers to any compounds which are formed by the linkage of two amino acids via a peptide bond and includes derivatives of such compounds.

The expression "phenylalanine, glutamine, valine, tyrosine, methionine, serine or threonine residue" used herein refers to a structural moiety of phenylalanine, glutamine, valine, tyrosine, methionine, serine or threonine that is freed of one $H_2O$ molecule, and this structural moiety constitutes a structural unit of a dipeptide.

The term "$^{13}C$-labeled alanine molecule" used herein refers to an alanine molecule in which at least one of the carbon atoms is replaced with a $^{13}C$ atom and thus the ratio of $^{13}C$ in the carbon atoms has been increased compared to the natural abundance of $^{13}C$.

The diagnostic agent of the invention for pancreatic exocrine function comprises a dipeptide represented by the following formula (I) or a pharmaceutically acceptable salt thereof.

$$X_1—R_1—Y_1 \quad (I)$$

wherein $X_1$ is a protecting group, $R_1$ is a phenylalanine, glutamine, valine, tyrosine, methionine, serine or threonine residue, and $Y_1$ is a $^{13}C$-labeled alanine molecule optionally having a protecting group.

In formula (I), $X_1$ is a protecting group. The protecting group includes any protecting groups which are generally used in the field of organic chemistry, for example, those described in "Textbook for Biochemical Experiments 1—Protein Chemistry IV", edited by Japan Biochemical Society, published by Tokyo Kagaku Dojin (1977); "Textbook for Experimental Chemistry 22—Organic Synthesis IV", edited by Japan Chemical Society, published by Maruzen (1992); "Fundamentals and Experiments of Peptide Synthesis", Nobuo Izumiya, Tetsuo Kato, Tohiko Aoyagi and Michinori Waki, published by Maruzen (1985); "Modification of Proteins", edited by Robert E. Feeney & John R. Whitaker, the American Chemical Society (1982); M. Bodanszky, "Principles of Peptides Synthesis", Springer-Verlag, Berlin (1984); and E. Schroder & K. Lubke, "The Peptides", Academic Press, N.Y. Vol. 1 (1965), Vol. 2 (1966). Specific examples of the protecting group include benzoyl, acetyl, benzyloxycarbonyl, substituted benzyloxycarbonyl (such as p-nitrobenzyloxycarbonyl, p-methoxybenzyloxycarbonyl, etc.), t-butyloxycarbonyl, 9-fluorenylmethoxycarbonyl, p-toluenesulfonyl, phthalyl, formyl, trifluoroacetyl, triphenylmethyl, cyclohexyloxycarbonyl, o-nitrophenylsulfenyl, t-acyloxycarbonyl, isobornyloxycarbonyl, diphenylphosphinyl, diphenylphosphinothioyl, benzyl, alkyl and allylthiocarbonyl, o-nitrophenoxyacetyl and chloroacetyl, benzenesulfonyl, dibenzylphosphoryl, trialkylsilyl, allylidene, and acetoacetyl.

Preferable examples of $X_1$ include benzoyl, acetyl, benzyloxycarbonyl and t-butyloxycarbonyl.

$R_1$ is a phenylalanine, glutamine, valine, tyrosine, methionine, serine or threonine residue.

$Y_1$ is a $^{13}C$-labeled alanine molecule optionally having a protecting group. The protecting group includes any protecting groups which are generally used in the field of organic chemistry, for example, those described in "Textbook for Biochemical Experiments 1—Protein Chemistry IV", edited by Japan Biochemical Society, published by Tokyo Kagaku Dojin (1977); "Textbook for Experimental Chemistry 22—Organic Synthesis IV", edited by Japan Chemical Society, published by Maruzen (1992); "Fundamentals and Experiments of Peptide Synthesis", Nobuo Izumiya, Tetsuo Kato, Tohiko Aoyagi and Michinori Waki, published by Maruzen (1985); "Modification of Proteins", edited by Robert E. Feeney & John R. Whitaker, the American Chemical Society (1982); M. Bodanszky, "Principles of Peptides Synthesis", Springer-Verlag, Berlin (1984); and E. Schroder & K. Lubke, "The Peptides", Academic Press, N.Y. Vol. 1 (1965), Vol. 2 (1966). Specifically, examples of protecting groups for carboxyl group include methyl ester, ethyl ester, benzyl ester, t-butyl ester, p-nitrobenzyl ester and N'-substituted hydrazide.

The amino acids represented by $R_1$ and $Y_1$ may be modified in various manners. Specific examples of such modification include guanidylation, succinylation and acetylation of amino groups; esterification of carboxyl groups; formation of sulfonium salts of methionine; and nitration and iodination of tyrosine.

Specific examples of pharmaceutically acceptable salts of the dipeptide represented by formula (I) include salts formed with inorganic acids such as hydrochloric acid, sulfuric acid, nitric acid or phosphoric acid; salts formed with organic acids such as acetic acid, propionic acid, succinic acid, malic acid, tartaric acid, citric acid or maleic acid; salts formed with alkali metals such as sodium or potassium; and salts formed with alkaline earth metals such as calcium.

The present invention also encompasses dipeptides represented by the following formula (II) or pharmaceutically acceptable salts thereof.

$$X_2—R_2—Y_2 \quad (II)$$

wherein $X_2$ is a protecting group, $R_2$ is a phenylalanine, glutamine, valine, tyrosine, methionine, serine or threonine residue, and $Y_2$ is a $^{13}$C-labeled alanine molecule optionally having a protecting group.

In formula (II), $X_2$ is a protecting group. The protecting group includes any protecting groups which are generally used in the field of organic chemistry, for example, those described in "Textbook for Biochemical Experiments 1—Protein Chemistry IV", edited by Japan Biochemical Society, published by Tokyo Kagaku Dojin (1977); "Textbook for Experimental Chemistry 22—Organic-Synthesis IV", edited by Japan Chemical Society, published by Maruzen (1992); "Fundamentals and Experiments of Peptide Synthesis", Nobuo Izumiya, Tetsuo Kato, Tohiko Aoyagi and Michinori Waki, published by Maruzen (1985); "Modification of Proteins", edited by Robert E. Feeney & John R. Whitaker, the American Chemical Society (1982); M. Bodanszky, "Principles of Peptides Synthesis", Springer-Verlag, Berlin (1984); and E. Schroder & K. Lubke, "The Peptides", Academic Press, N.Y. Vol. 1 (1965), Vol. 2 (1966). Specific examples of the protecting group include benzoyl, acetyl, benzyloxycarbonyl, substituted benzyloxycarbonyl (such as p-nitrobenzyloxycarbonyl, p-methoxybenzyloxycarbonyl, etc.), t-butyloxycarbonyl, 9-fluorenylmethoxycarbonyl, p-toluenesulfonyl, phthalyl, formyl, trifluoroacetyl, triphenylmethyl, cyclohexyloxycarbonyl, o-nitrophenylsulfenyl, t-acyloxycarbonyl, isobornyloxycarbonyl, diphenylphosphinyl, diphenylphosphinothioyl, benzyl, alkyl and allylthiocarbonyl, o-nitrophenoxyacetyl and chloroacetyl, benzenesulfonyl, dibenzylphosphoryl, trialkylsilyl, allylidene, and acetoacetyl.

Preferable examples of $X_2$ include benzoyl, acetyl, benzyloxycarbonyl and t-butyloxycarbonyl.

$R_2$ is a phenylalanine, glutamine, valine, tyrosine, methionine, serine or threonine residue.

$Y_2$ is a $^{13}$C-labeled alanine molecule optionally having a protecting group. The protecting group includes any protecting groups which are generally used in the field of organic chemistry, for example, those described in "Textbook for Biochemical Experiments 1—Protein Chemistry IV", edited by Japan Biochemical Society, published by Tokyo Kagaku Dojin (1977); "Textbook for Experimental Chemistry 22—Organic Synthesis IV", edited by Japan Chemical Society, published by Maruzen (1992); "Fundamentals and Experiments of Peptide Synthesis", Nobuo Izumiya, Tetsuo Kato, Tohiko Aoyagi and Michinori Waki, published by Maruzen (1985); "Modification of Proteins", edited by Robert E. Feeney & John R. Whitaker, the American Chemical Society (1982); M. Bodanszky, "Principles of Peptides Synthesis", Springer-Verlag, Berlin (1984); and E. Schroder & K. Lubke, "The Peptides", Academic Press, N.Y. Vol. 1 (1965), Vol. 2 (1966). Specifically, examples of protecting groups for carboxyl group include methyl ester, ethyl ester, benzyl ester, t-butyl ester, p-nitrobenzyl ester and N'-substituted hydrazide.

The amino acids represented by $R_2$ and $Y_2$ may be modified in various manners. Specific examples of such modification include guanidylation, succinylation and acetylation of amino groups; esterification of carboxyl groups; formation of sulfonium salts of methionine; and nitration and iodination of tyrosine.

Specific examples of pharmaceutically acceptable salts of the dipeptide represented by formula (II) include salts formed with inorganic acids such as hydrochloric acid, sulfuric acid, nitric acid or phosphoric acid; salts formed with organic acids such as acetic acid, propionic acid, succinic acid, malic acid, tartaric acid, citric acid or maleic acid; salts formed with alkali metals such as sodium or potassium; and salts formed with alkaline earth metals such as calcium.

In a preferred embodiment of the present invention, the $^{13}$C-labeled dipeptide represented by formula (I) and the $^{13}$C-labeled dipeptide represented by formula (II) are selected from the group consisting of the following compounds:

(a) Bz-Phe-($^{13}$C-Ala)
(b) Bz-Gln-($^{3}$C-Ala),
(c) Bz-Val-($^{13}$C-Ala),
(d) Bz-Tyr-($^{13}$C-Ala),
(e) Bz-Met-($^{13}$C-Ala),
(f) Bz-Ser-($^{13}$C-Ala),
(g) Bz-Thr-($^{13}$C-Ala),
(h) Ac-Met-($^{13}$C-Ala),
(i) Z-Met-($^{13}$C-Ala),
(j) Boc-Met-($^{13}$C-Ala), and
(k) Boc-Phe-($^{13}$C-Ala)

wherein Bz is benzoyl, Ac is acetyl, Z is benzyloxycarbonyl, and Boc is t-butyloxycarbonyl.

The $^{13}$C-labeled dipeptide represented by the above formula (I) and pharmaceutically acceptable salts thereof and the $^{13}$C-labeled dipeptide represented by the above formula (II) and pharmaceutically acceptable salts thereof are absorbed through the digestive tract upon reaction with pancreatic exocrine protease(s), and decarboxylated by metabolic action to generate $^{13}CO_2$. Examples of pancreatic exocrine proteases include chymotrypsin, trypsin, elastase, and carboxypeptidases represented by carboxypeptidase A and B.

The $^{13}$C-labeled dipeptides described above may be synthesized by conventional methods using commercially available amino acids. For example, methods described in "Textbook for Experimental Chemistry 22—Organic Synthesis IV", edited by Japan Chemical Society, published by Maruzen (1992) may be used. One illustrative example thereof will be described below.

$^{13}$C-labeled alanine is dissolved in hydrogen chloride/methanol and refluxed. The resulting methyl ester is suspended in dichloromethane, and then triethylamine is added thereto dropwise while ice-cooling and agitating. Further, N-benzoyl-amino acid, HOBt (1-hydroxy-1H-benzotriazole.$H_20$) and dichloromethane are added thereto. Then, a solution of WSC (1-ethyl-3-(3-dimethylaminopropyl)-carbodiimide HCl) dissolved in dichloromethane is added thereto and agitated. After concentration, the reaction solution is extracted with ethyl acetate, washed with 1N HCl, 5% $NaHCO_3$ and water, dried over magnesium sulfate, and evaporated to dryness, or further saponified, to yield the desired $^{13}C$-labeled compound represented by the above formula (I) or (II).

The $^{13}C$-labeled dipeptide may be obtained in the form of a salt. The salt may include those with inorganic acids such as hydrochloric, sulfuric, nitric and phosphoric acids; those with organic acids such as formic, acetic, propionic, glycolic, succinic, malic, tartaric, citric and trifluoroacetic acids; those with alkali metals such as sodium and potassium; those with alkaline earth metals such as calcium; and those with organic amines such as ammonium, ethanolamine, triethylamine and dicyclohexylamine.

Tests using the diagnostic agent for pancreatic exocrine function according to the present invention are carried out by administering to a subject the $^{13}C$-labeled dipeptide represented by formula (I) or a pharmaceutically acceptable salt thereof. Although tests are possible in which the concentration of the $^{13}C$-labeled compound is measured in serum, urine or stool after the administration, breath tests are desirable in which an increase in $^{13}C$ concentration in the exhaled $CO_2$ is measured after the administration. When the $^{13}C$-labeled dipeptide represented by formula (I) or a pharmaceutically acceptable salt thereof is administered to a subject, the subject may be fed with a test meal or the like to induce secretion of pancreatic enzymes. Also, two or more $^{13}C$-labeled compounds represented by formula (I) or pharmaceutically acceptable salts thereof may be combined for use. Specifically, when a $^{13}C$-labeled compound is used, $^{13}C$ concentrations in the exhaled $CO_2$ are determined after the administration. Then, the pancreatic exocrine function is diagnosed from either the data on the degree of increase of the $^{13}C$ concentration in the exhaled $CO_2$ ($\Delta^{13}C$(‰)) at predetermined time points (e.g., 5, 10 or 15 min after the administration), or the data on the time course of the degree of increase of the $^{13}C$ concentration in the exhaled $CO_2$ ($\Delta^{13}C$(‰)) up to a predetermined time point after the administration (i.e., onset slope, change in slope, peak time, etc.). These test methods utilize the phenomenon that when the $^{13}C$-labeled dipeptide represented by formula (I) or pharmaceutically acceptable salt thereof is administered to a subject, the compound is absorbed through the digestive tract upon reaction with pancreatic exocrine proteases, and decarboxylated by metabolic action in the body to generate $^{13}CO_2$.

The $^{13}C$ concentration in the exhaled $^{13}CO_2$ can be determined by gas chromatography-mass spectrometry (GC-MS), infrared spectroscopy, mass spectrometry, photoelectric acoustic spectroscopy, NMR (nuclear magnetic resonance), and other methods.

The diagnostic agent for pancreatic exocrine function according to the present invention may be formulated from the $^{13}C$-labeled dipeptide represented by formula (I) or pharmaceutically acceptable salt thereof, either alone or in combination with an excipient or carrier, into an oral preparation such as tablets, capsules, a powder, granules, a liquid, etc. The excipient or carrier may be any pharmaceutically acceptable excipients or carriers that are conventionally used in this field, and their nature and composition may be appropriately chosen. For example, water may be used as a liquid carrier. Solid carriers include cellulose derivatives such as hydroxypropyl cellulose, and organic acid salts such as magnesium stearate. Also, the diagnostic agent of the invention may be used as a freeze-dried preparation.

The $^{13}C$-labeled dipeptide represented by formula (I) or pharmaceutically acceptable salt thereof is contained in preparations in variable amounts depending on the kind of the preparation, but generally in an amount of 1 to 100% by weight, preferably 50 to 100% by weight. In capsule, tablet, granule or powder preparations, the $^{13}C$-labeled dipeptide represented by formula (I) or pharmaceutically acceptable salt thereof is contained in the preparation in an amount of about 10 to 100% by weight, preferably 50 to 100% by weight, the remainder being a carrier.

The dose of the diagnostic agent for pancreatic exocrine function according to the present invention should be sufficient to enable confirming an increase of $^{13}CO_2$ in the breath caused by its administration. The dose will vary depending upon the age and body weight of the patient and the purpose of the test. For example, the dose per test may be about 1 to 1000 mg/kg of body weight for an adult.

The present specification encompasses the contents of the specification and/or drawings of Japanese Patent Application No. 2001-243142 based on which the present application claims priority.

Ala)-ONa was administered orally to chronic pancreatitis rats (●, n=10) and normal rats (■, n=5) at 13.2 mg/kg. The error bars represent SD.

Figure 16:
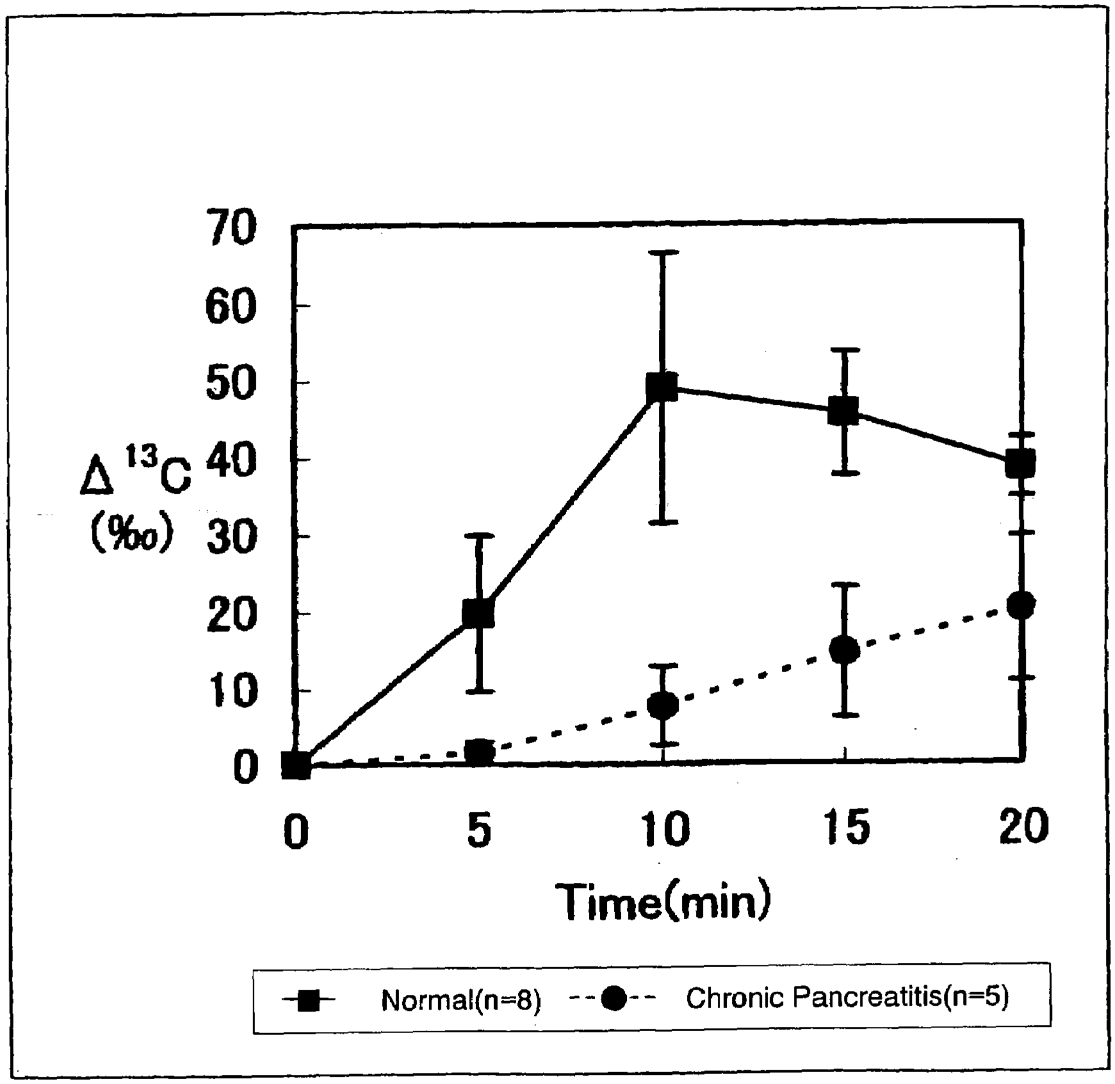

FIG. 16 shows the time course of the degree of increase of $^{13}C$ concentration in exhaled $CO_2$ ($\Delta^{13}C$(‰)) after administration of Bz-Met-($^{13}C$-Ala)-ONa. At 0 min, Bz-Met-($^{13}C$-Ala)-ONa was administered orally to chronic pancreatitis rats (●, n=5) and normal rats (■, n=8) at 12.1 mg/kg. The error bars represent SD.

Figure 17:
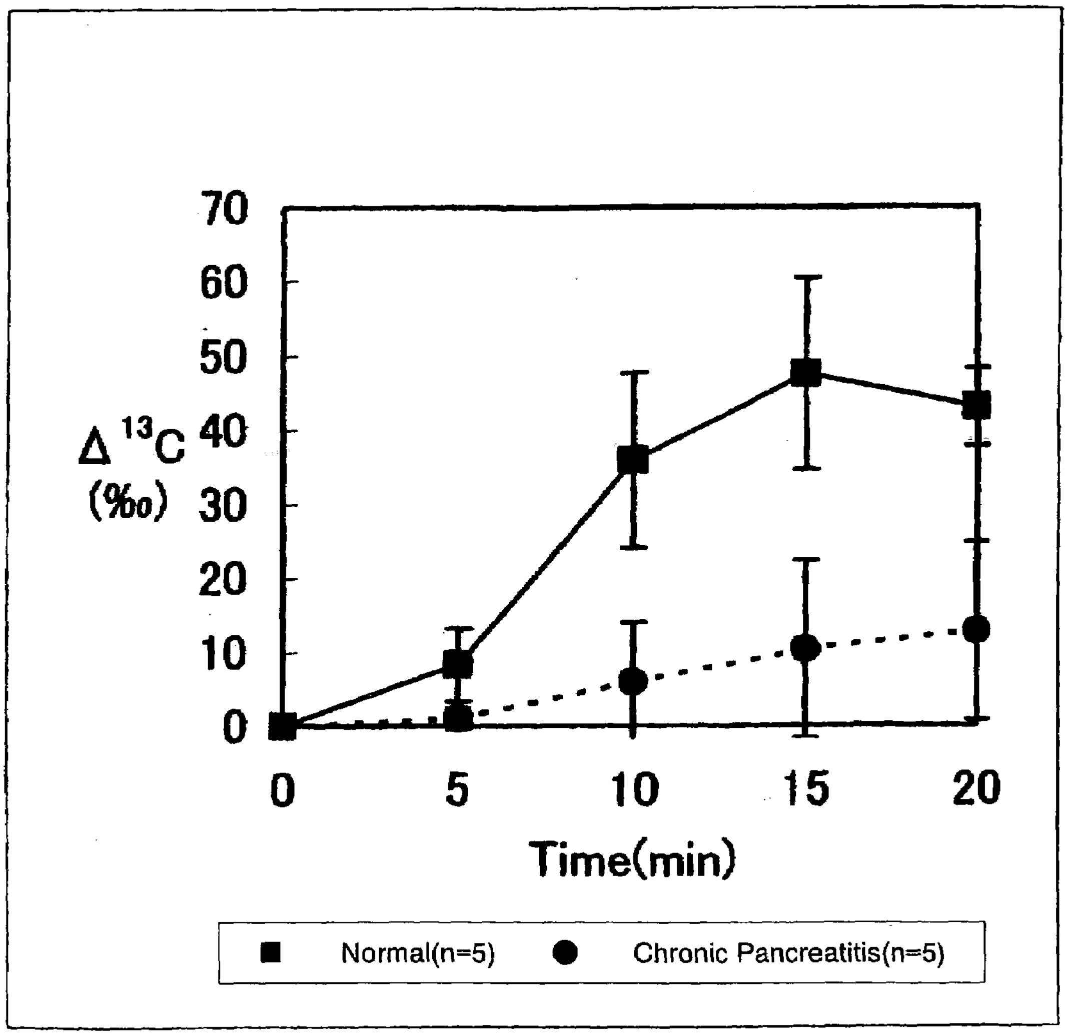

FIG. 17 shows the time course of the degree of increase of $^{13}C$ concentration in exhaled $CO_2$ ($\Delta^{13}C$(‰)) after administration of Bz-Ser-($^{13}C$-Ala)-ONa. At 0 min, Bz-Ser-($^{13}C$-Ala)-ONa was administered orally to chronic pancreatitis rats (●, n=5) and normal rats (■, n=5) at 10.6 mg/kg. The error bars represent SD.

Figure 18:
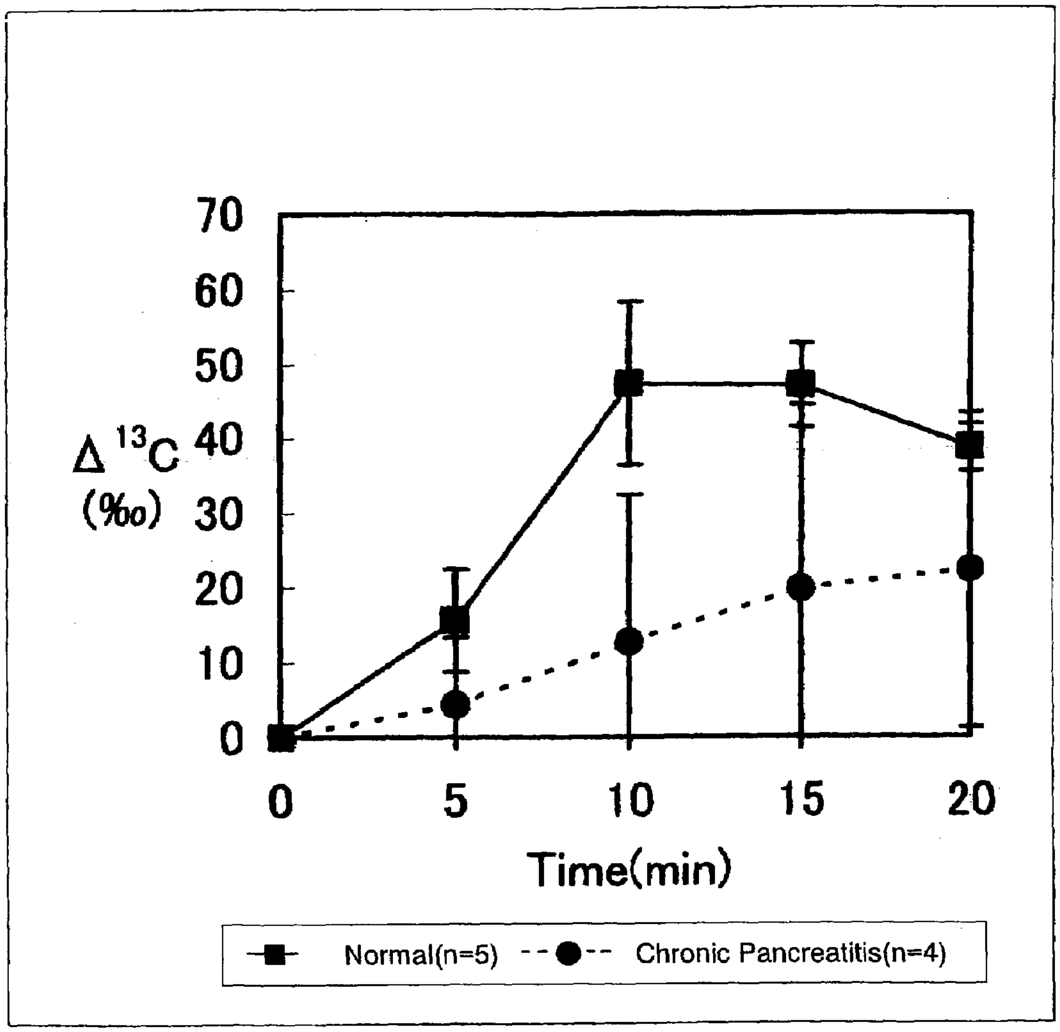

FIG. 18 shows the time course of the degree of increase of $^{13}C$ concentration in exhaled $CO_2$ ($\Delta^{13}C$(‰)) after administration of Bz-Thr-($^{13}C$-Ala)-ONa. At 0 min, Bz-Thr-($^{13}C$-Ala)-ONa was administered orally to chronic pancreatitis rats (●, n=4) and normal rats (■, n=5) at 11.0 mg/kg. The error bars represent SD.

Figure 19:
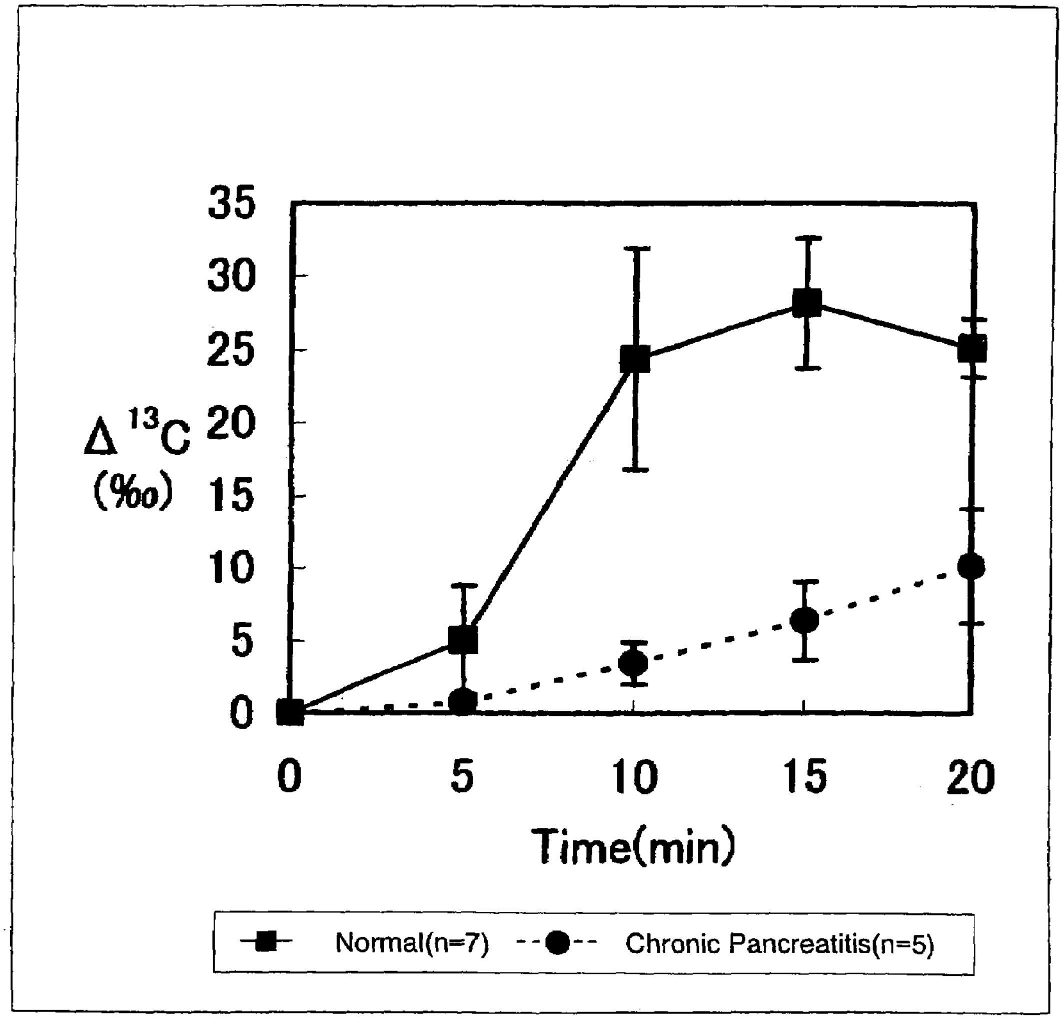

FIG. 19 shows the time course of the degree of increase of $^{13}C$ concentration in exhaled $CO_2$ ($\Delta^{13}C$(‰)) after administration of Boc-Phe-($^{13}C$-Ala)-ONa. At 0 min, Boc-Phe-($^{13}C$-Ala)-ONa was administered orally to chronic pancreatitis rats (●, n=5) and normal rats (■, n=7) at 8.84 mg/kg. The error bars represent SD.

BEST MODES FOR CARRYING OUT THE INVENTION

Hereinbelow, the present invention will be illustrated in more detail with reference to Examples. However, the scope of the present invention shall not be limited by those Examples. In the following Examples, amino acid residues shown in three-letter abbreviations are L-isomers unless otherwise specified.

EXAMPLE 1

Preparation of N-benzoyl-L-phenylalanyl-$^{13}C$-L-alanine (Bz-Phe-($^{13}C$-Ala)) and its Sodium Salt $^{13}C$-Alanine (Masstrace, Inc.) (10.0 g, 0.111 mol) was dissolved in aqueous sodium hydroxide (111 ml). To this solution, $Boc_2O$ (28.0 ml, 0.122 mol) in acetone (110 ml) and triethylamine (7.71 ml, 55.5 mmol) were added and agitated overnight at room temperature. After concentration under reduced pressure, saturated aqueous sodium chloride was added to give a 200 ml solution. Citric acid was added thereto to adjust the pH at 4, followed by saturation of the solution with sodium chloride. Then, the resultant solution was extracted with ethyl acetate four times. The organic layer was washed with saturated aqueous sodium chloride twice, and dried over anhydrous magnesium sulfate. After concentration under reduced pressure, the resultant material was dissolved in diethyl ether (150 ml). Then, cyclohexylamine (12.7 ml, 0.111 mol) was added thereto and the solution was left stationary for 2 hr at room temperature. The crystals deposited were filtered out, washed with diethyl ether, and dried under reduced pressure to yield Boc-($^{13}C$-Ala)-OH.CHA.

To a suspension of Boc-($^{13}C$-Ala)-OH.CHA (32.08 g, 0.111 mol) in ethyl acetate (400 ml), 10% aqueous citric acid (100 ml) was added and agitated at room temperature. When the suspension turned into a solution, it was saturated with sodium chloride to separate the organic layer. After two extractions with ethyl acetate, the organic layers were combined and washed with aqueous saturated sodium chloride twice. The resultant material was dried over anhydrous magnesium sulfate and then concentrated under reduced pressure to yield a colorless extract. This extract was dissolved in ethanol/water (9:1) (200 ml), followed by addition of cesium carbonate (19.0 g, 58.3 mmol). When foaming stopped, the solution was concentrated under reduced pressure. Toluene was added to the residue, and water was removed by azeotropic distillation to thereby obtain a gel-like material. This material was suspended in DMF (200 ml), and benzyl bromide (13.2 ml, 0.111 mol) was added thereto and agitated for 12 hr at room temperature. After concentration under reduced pressure, ethyl acetate was added to the residue, which was then washed with water, 10% aqueous citric acid, saturated aqueous sodium chloride, saturated aqueous sodium hydrogencarbonate and saturated aqueous sodium chloride in this order and dried over anhydrous magnesium sulfate. Ethyl acetate was distilled off under reduced pressure to yield Boc-($^{13}C$-Ala)-OBzl.

4.5 N hydrogen chloride/dioxane (250 ml) was added to Boc-($^{13}C$-Ala)-OBzl (31.27 g, 0.111 mol), and the resultant solution was left stationary for 30 min at room temperature. After concentration under reduced pressure, diethyl ether (200 ml) was added thereto. The deposited crystals were filtered out and dried under reduced pressure to yield 22.48 g of HCl.H-($^{13}C$-Ala)-OBzl.

HCl.H-($^{13}C$-Ala)-OBzl (700 mg, 3.2 mmol), Boc-Phe (Peptide Institute Inc.) (857 mg, 3.23 mmol) and HOBt (458 mg, 3.39 mmol) were dissolved in DMF (10 ml). To this solution, WSCD (620 μl, 3.39 mmol) was added dropwise while ice-cooling and agitating, followed by agitation for 2 hr at room temperature. After addition of ethyl acetate, the reaction product was washed with saturated aqueous sodium hydrogencarbonate, saturated aqueous sodium chloride, 10% aqueous citric acid, and saturated aqueous sodium chloride in this order. After drying over anhydrous sodium sulfate, ethyl acetate was distilled off under reduced pressure to yield Boc-Phe-($^{13}C$-Ala)-OBzl.

4.5 N hydrogen chloride/dioxane (30 ml) was added to Boc-Phe-($^{13}C$-Ala)-OBzl (1.30 g, 3.04 mmol), and the resultant solution was left stationary for 1 hr at room temperature. After concentration under reduced pressure, the solution was further dried under reduced pressure. The resultant material was dissolved in DMF (10 ml). To this solution, benzoic acid (371 mg, 3.04 mmol) and HOBt (411 mg, 3.04 mmol) were added while ice-cooling and agitating. Then, WSCD (547 μl, 3.04 mmol) was added dropwise, and the solution was agitated for 2 hr at room temperature. After addition of ethyl acetate, the reaction product was washed with saturated aqueous sodium hydrogencarbonate, saturated aqueous sodium chloride, 10% aqueous citric acid, and saturated aqueous sodium chloride in this order, and then dried over anhydrous sodium sulfate. After concentration under reduced pressure, isopropyl ether was added for crystallization to yield Bz-Phe-($^{13}C$-Ala)-OBzl.

Bz-Phe-($^{13}C$-Ala)-OBzl (1.13 g, 2.62 mmol) was dissolved in acetic acid (50 ml). After addition of 5% palladium carbon (500 mg) to this solution, hydrogen gas was blown thereinto for 2 hr while agitating at room temperature. After the catalyst was filtered out, acetic acid was distilled off. Ethyl acetate was added to the resultant material, which was then washed with saturated aqueous hydrogen chloride and dried over anhydrous sodium sulfate. After concentration under reduced pressure, isopropyl ether was added to solidify the concentrated material. Then, water (50 ml) was added to prepare a suspension, which was lyophilized to yield Bz-Phe-($^{13}$C-Ala)-OH.0.25$H_2O$.

Bz-Phe-($^{13}$C-Ala)-OH.0.25$H_2O$ (755 mg, 2.185 mmol) was dissolved in 30% aqueous acetonitrile (30 ml). To this solution, 1 M aqueous sodium carbonate (1.093 ml, 2.185 mmol) was added. When foaming stopped, the solution was lyophilized to yield 747 mg of Bz-Phe-($^{13}$C-Ala)-ONa.

Figure 1:
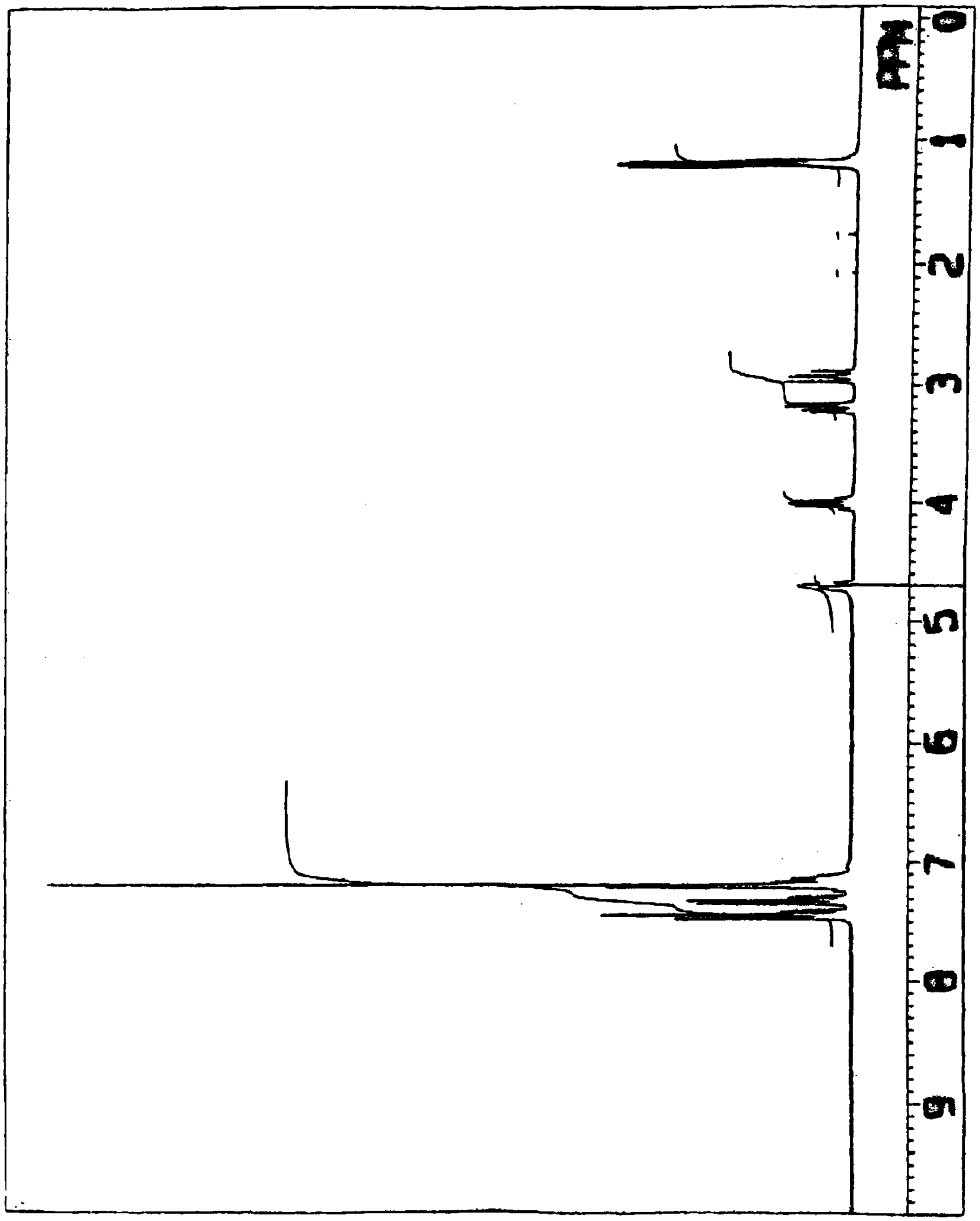
FIG. 1 shows the $^1H$-NMR spectrum (in $D_2O$) of Bz-Phe-($^{13}C$-Ala)-ONa.

The confirmation of the structure of the resultant compound and the analysis of the $^{13}$C-labeled position were performed by $^1$H-NMR (FIG. 1), $^{13}$C-NMR and mass spectrometry.

$^{13}$C-NMR (in $D_2O$): 180.6 ppm

Mass spectrometry (MALDI-MS): 364.3 (M+Na)

EXAMPLE 2

Preparation of N-benzoyl-L-glutaminyl-$^{13}$C-L-alanine (Bz-Gln-($^{13}$C-Ala)) and its Sodium Salt HCl.H-($^{13}$C-Ala)-OBzl (450 mg, 2.07 mmol) obtained in the same manner as in Example 1, Boc-Gln (Peptide Institute Inc.) (510 mg, 2.07 mmol) and HOBt (294 mg, 2.17 mmol) were dissolved in DMF (5 ml). To this solution, WSCD (385 μl, 2.17 mmol) was added dropwise while ice-cooling and agitating, followed by agitation for 30 min under ice-cooling and for 2 hr at room temperature. After addition of ethyl acetate, the reaction product was washed with saturated aqueous sodium hydrogencarbonate, saturated aqueous sodium chloride, 10% aqueous citric acid, and saturated aqueous sodium chloride in this order, and then dried over anhydrous magnesium sulfate. The ethyl acetate was distilled off under reduced pressure. Then, hexane was added to the solution for crystallization to yield Boc-Gln-($^{13}$C-Ala)-OBzl.

4.5 N hydrogen chloride/dioxane (30 ml) was added to Boc-Gln-($^{13}$C-Ala)-OBzl (1300 mg, 3.18 mmol), and the resultant solution was left stationary for 1 hr at room temperature. After concentration under reduced pressure, the solution was further dried under reduced pressure. The resultant material was dissolved in DMF (10 ml). To this solution, benzoic acid (402 mg, 3.30 mmol) and HOBt (468 mg, 3.46 mmol) were added while ice-cooling and agitating. Then, WSCD (633 μl, 3.46 mmol) was added dropwise, and the solution was agitated for 2 hr at room temperature. Water was added thereto, and the deposited solid was filtered out and washed with water. The resultant material was re-precipitated with methanol/ether and filtered out to yield Bz-Gln-($^{13}$C-Ala)-OBzl.

Bz-Gln-($^{13}$C-Ala)-OBzl (890 mg, 2.16 mmol) was dissolved in acetic acid (50 ml). After addition of 5% palladium carbon (500 mg) to this solution, hydrogen gas was blown thereinto for 2 hr while agitating at room temperature. After the catalyst was filtered off, acetic acid was distilled off. Acetonitrile/water was added to the resultant residue, which was then lyophilized to yield Bz-Gln-($^{13}$C-Ala)-OH.

To Bz-Gln-($^{13}$C-Ala)-OH (618 mg, 1.917 mmol), water (10 ml) was added. Then, 1 M aqueous sodium carbonate (1054 μl, 2.108 mmol) was added thereto. When foaming stopped, the solution was purified by RP-HPLC (YMC-PAK ODS 10 μm, 30×250 mm, 5–20% MeCN, 60 min, 20 ml/min). The major fractions were lyophilized to yield 544 mg of Bz-Gln-($^{13}$C-Ala)-ONa.

Figure 2:
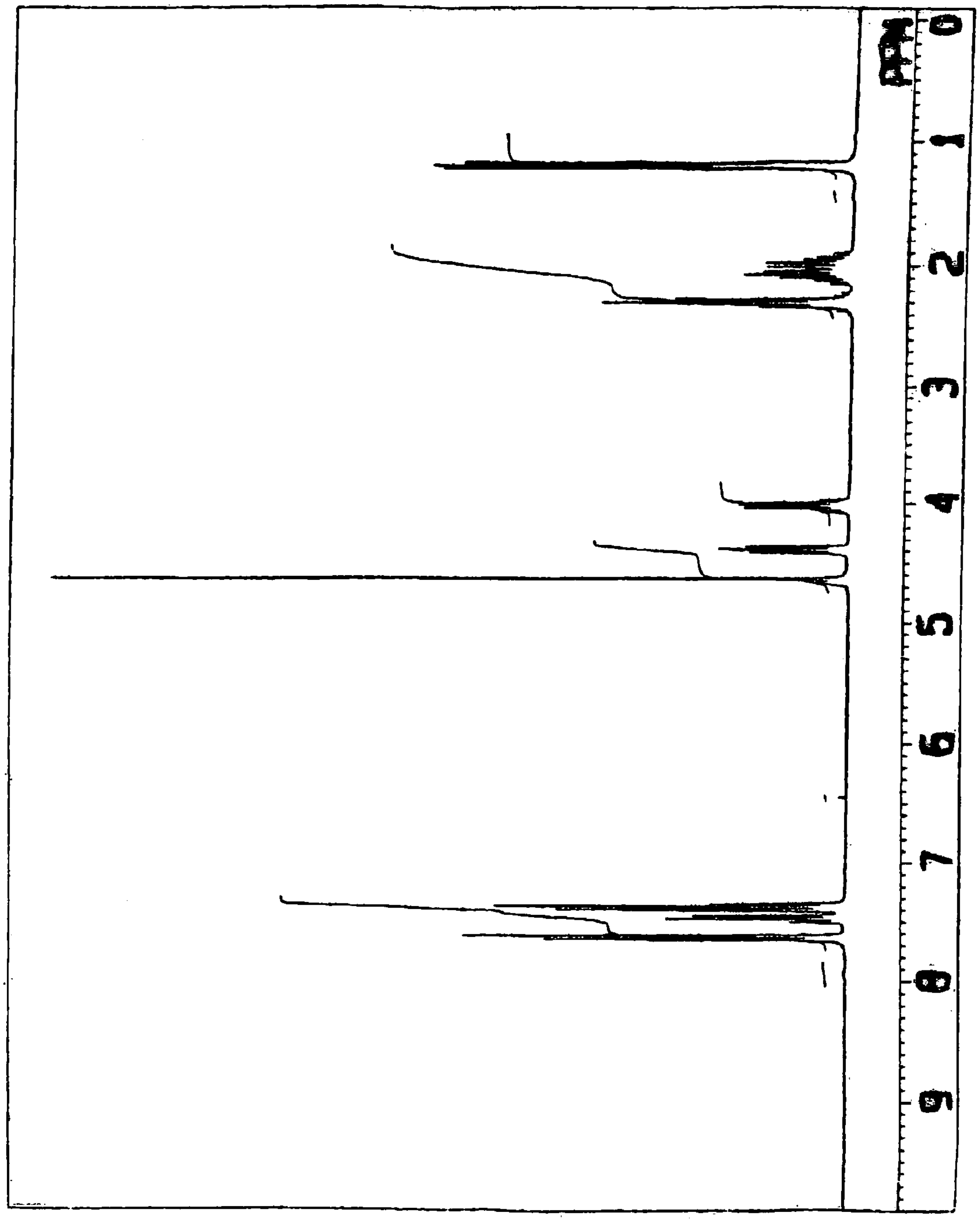
FIG. 2 shows the $^1H$-NMR spectrum (in $D_2O$) of Bz-Gln-($^{13}C$-Ala)-ONa.

The confirmation of the structure of the resultant compound and the analysis of the $^{13}$C-labeled position were performed by $^1$H-NMR (FIG. 2), $^{13}$C-NMR and mass spectrometry.

$^{13}$C-NMR (in $D_2O$): 180.8 ppm

Mass spectrometry (MALDI-MS): 345.1 (M+Na)

EXAMPLE 3

Preparation of N-benzoyl-L-valyl-$^{13}$C-L-alanine (Bz-Val-($^{13}$C-Ala)) and its Sodium Salt HCl.H-($^{13}$C-Ala)-OBzl (700 mg, 3.23 mmol) obtained in the same manner as in Example 1, Boc-Val (Peptide Institute Inc.) (702 mg, 3.23 mmol) and HOBt (458 mg, 3.39 mmol) were dissolved in DMF (10 ml). To this solution, WSCD (620 μl, 3.39 mmol) was added dropwise while ice-cooling and agitating, followed by agitation for 2 hr at room temperature. After addition of ethyl acetate, the reaction product was washed with saturated aqueous sodium hydrogencarbonate, water, 10% aqueous citric acid, and water in this order. Then, the solution was dried over anhydrous sodium sulfate, and the ethyl acetate was distilled off under reduced pressure. The residue was solidified with diethyl ether, filtered out, and dried under reduced pressure to yield Boc-Val-($^{13}$C-Ala)-OBzl.

4.5 N hydrogen chloride/dioxane (30 ml) was added to Boc-Val-($^{13}$C-Ala)-OBzl (1.26 g, 3.32 mmol), and the resultant solution was left stationary for 1 hr at room temperature. After concentration under reduced pressure, the solution was further dried under reduced pressure. The resultant material was dissolved in DMF (10 ml). To this solution, benzoic acid (405 mg, 3.32 mmol) and HOBt (449 mg, 3.32 mmol) were added while ice-cooling and agitating. Then, WSCD (608 μl, 3.32 mmol) was added dropwise, and the solution was agitated for 2 hr at room temperature. After addition of ethyl acetate, the reaction product was washed with saturated aqueous sodium hydrogencarbonate, saturated aqueous sodium chloride, 10% aqueous citric acid, and saturated aqueous sodium chloride in this order, and then dried over anhydrous sodium sulfate. After concentration under reduced pressure, isopropyl ether was added for crystallization to yield Bz-Val-($^{13}$C-Ala)-OBzl.

Bz-Val-($^{13}$C-Ala)-OBzl (960 mg, 2.50 mmol) was dissolved in acetic acid (50 ml). After addition of 5% palladium carbon (500 mg) to this solution, hydrogen gas was blown thereinto for 2 hr while agitating at room temperature. After the catalyst was filtered out, acetic acid was distilled off. Ethyl acetate was added to the resultant residue, which was then washed with saturated aqueous sodium chloride and dried over anhydrous sodium sulfate. After concentration under reduced pressure, isopropyl ether was added to solidify the resultant material. Then, water (50 ml) was added thereto to prepare a suspension, which was lyophilized to yield Bz-Val-($^{13}$C-Ala)-OH.0.32$H_2O$.

Bz-Val-($^{13}$C-Ala)-OH.0.32$H_2O$ (547 mg, 1.83 mmol) was dissolved in 30% aqueous acetonitrile (30 ml), and 1 M aqueous sodium carbonate (915 μl, 1.83 mmol) was added thereto. When foaming stopped, the solution was lyophilized to yield 561 mg of Bz-Val-($^{13}$C-Ala)-ONa.

Figure 3:
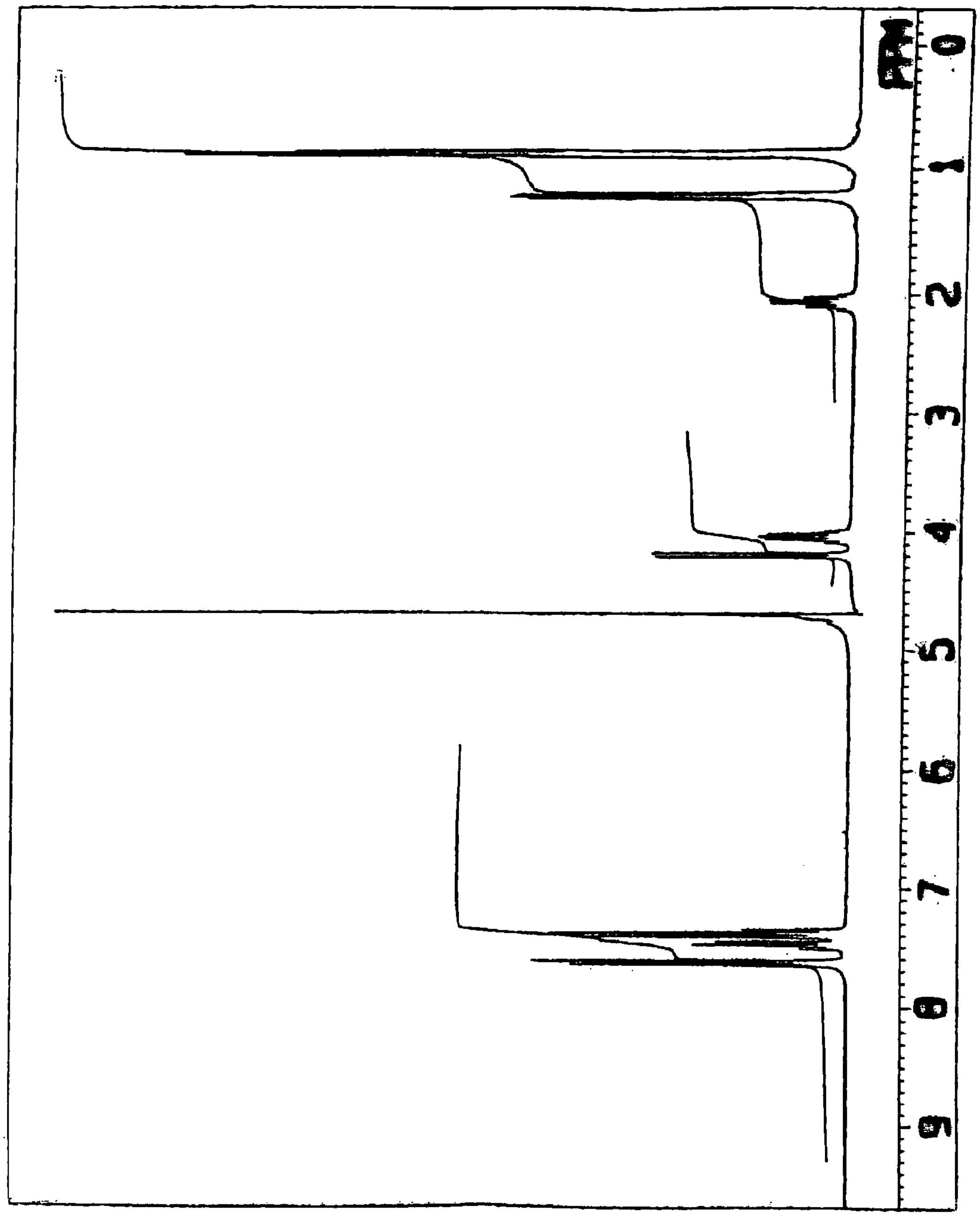
FIG. 3 shows the $^1H$-NMR spectrum (in $D_2O$) of Bz-Val-($^{13}C$-Ala)-ONa.

The confirmation of the structure of the resultant compound and the analysis of the $^{13}$C-labeled position were performed by $^1$H-NMR (FIG. 3), $^{13}$C-NMR and mass spectrometry.

$^{13}$C-NMR (in $D_2O$): 180.7 ppm

Mass spectrometry (MALDI-MS): 316.1 (M+Na)

EXAMPLE 4

Preparation of N-benzoyl-L-tyrosyl-$^{13}$C-L-alanine (Bz-Tyr-($^{13}$C-Ala)) and its Sodium Salt HCl.H-($^{13}$C-Ala)-OBzl (700 mg, 3.23 mmol) obtained in the same manner as in Example 1, Boc-Tyr(Brz) (Peptide Institute Inc.) (1.60 g, 3.23 mmol) and HOBt (459 mg, 3.39 mmol) were dissolved in DMF (8 ml). To this solution, WSCD (602 μl, 3.39 mmol) was added dropwise while ice-cooling and agitating, followed by agitation for 30 min under ice-cooling and for 2 hr at room temperature. After addition of ethyl acetate, the reaction product was washed with saturated aqueous sodium hydrogencarbonate, water, 10% aqueous citric acid, and water in this order and then dried over anhydrous sodium sulfate. The ethyl acetate was distilled off under reduced pressure, and the resultant crystalline residue was washed with diethyl ether, filtered out, and dried under reduced pressure to yield Boc-Tyr(Brz)-($^{13}$C-Ala)-OBzl.

6 N hydrogen chloride/dioxane (30 ml) was added to Boc-Tyr(Brz)-($^{13}$C-Ala)-OBzl (2.01 g, 3.06 mmol), and the resultant solution was agitated for 40 min at room temperature. After concentration under reduced pressure, the residue was dissolved in DMF (10 ml). To this solution, benzoic acid (378 mg, 3.09 mmol) and HOBt (434 mg, 3.37 mmol) were added. Then, WSCD (599 μl, 3.37 mmol) was added little by little, and the solution was agitated for 30 min under ice-cooling and for 2 hr at room temperature. After addition of ethyl acetate, the reaction product was washed with saturated aqueous sodium hydrogencarbonate, water, 10% aqueous citric acid, and water in this order, and then dried over anhydrous sodium sulfate. The ethyl acetate was distilled off under reduced pressure, and the resultant residue was washed with diethyl ether, filtered out and dried under reduced pressure to yield Bz-Tyr(Brz)-($^{13}$C-Ala)-OBzl.

To a mixture of Bz-Tyr(Brz)-($^{13}$C-Ala)-OBzl (1.81 g, 2.74 mmol) and anisole (3.0 ml, 27.8 mmol), anhydrous hydrogen fluoride (15 ml) was introduced while cooling in a dry ice/methanol bath under agitating. Then, the solution was agitated for 1 hr under ice-cooling. After the hydrogen fluoride was distilled off under ice-cooling, diisopropyl ether (30 ml) was added to filter out the insoluble matter. The insoluble matter was washed with diisopropyl ether and dried under reduced pressure to yield Bz-Tyr-($^{13}$C-Ala)-OH.

To an aqueous solution of Bz-Tyr-($^{13}$C-Ala)-OH (20 ml), 1 M aqueous sodium carbonate (3.40 ml, 3.40 mmol) was added to adjust the pH at 8. The trace insoluble matter was filtered off with a membrane filter. Then, the solution was purified by RP-HPLC (YMC-PAK ODS 10 μm, 30×250 mm, 1–60% MeCN, 80 min, 20 ml/min). The major fractions were collected and lyophilized to yield 731 mg of Bz-Tyr-($^{13}$C-Ala)-ONa.

Figure 4:
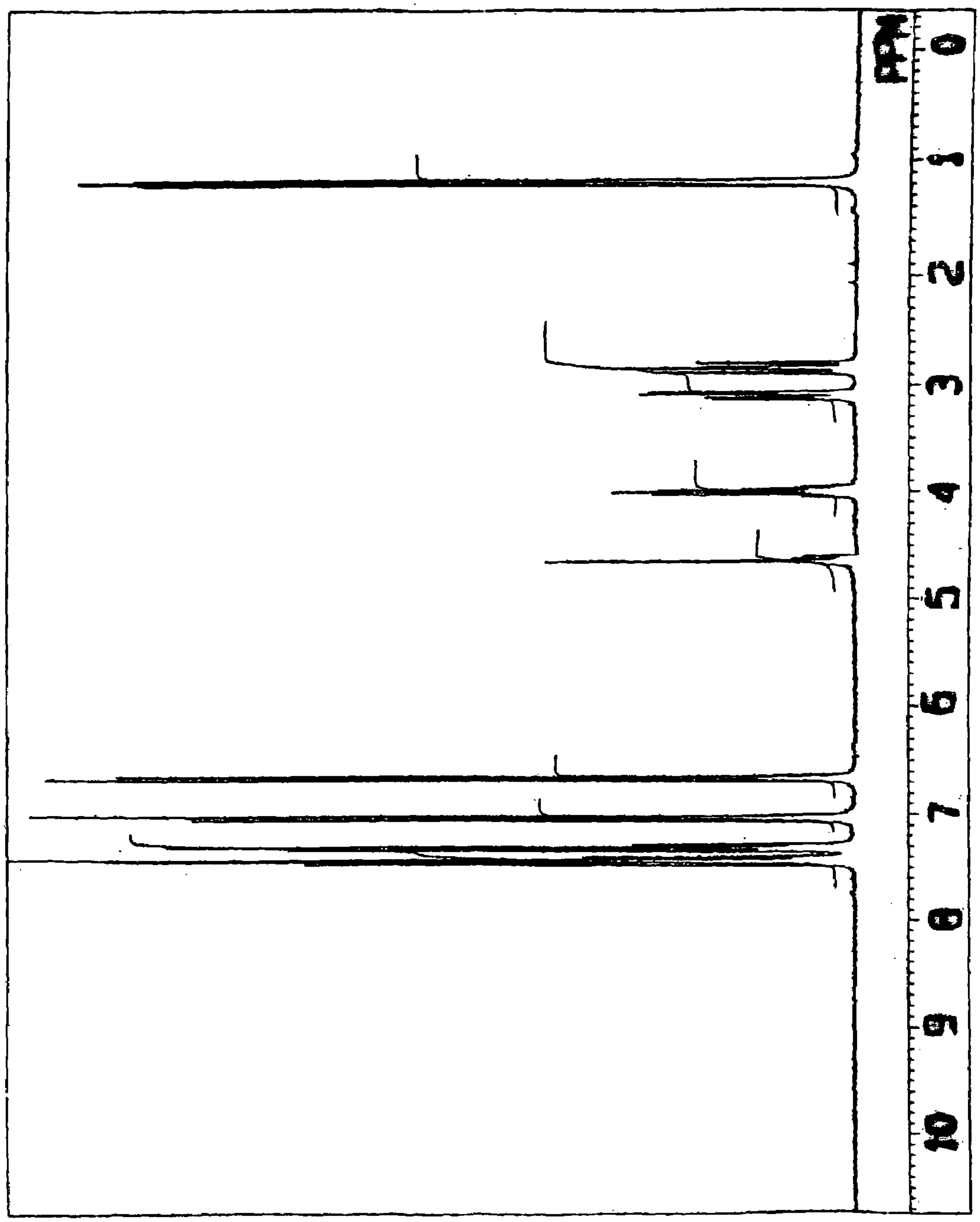
FIG. 4 shows the $^1H$-NMR spectrum (in $D_2O$) of Bz-Tyr-($^{13}C$-Ala)-ONa.

The confirmation of the structure of the resultant compound and the analysis of the $^{13}$C-labeled position were performed by $^1$H-NMR (FIG. 4), $^{13}$C NMR and mass spectrometry.

$^{13}$C-NMR (in $D_2O$): 180.6 ppm

Mass spectrometry (ESI-MS): 380.1 (M+Na)

EXAMPLE 5

Preparation of N-benzoyl-L-methionyl-$^{13}$C-L-alanine (Bz-Met-($^{13}$C-Ala)) and its Sodium Salt HCl.H-($^{13}$C-Ala)-OBzl (700 mg, 3.23 mmol) obtained in the same manner as in Example 1, Boc-Met (Peptide Institute Inc.) (805 mg, 3.23 mmol) and HOBt (459 mg, 3.39 mmol) were dissolved in DMF (8 ml). To this solution, WSCD (602 μl, 3.39 mmol) was added dropwise while ice-cooling and agitating, followed by agitation for 30 min under ice-cooling and for 3 hr at room temperature. After addition of ethyl acetate, the reaction product was washed with saturated aqueous sodium hydrogencarbonate, water, 10% aqueous citric acid, and water in this order and then dried over anhydrous sodium sulfate. The ethyl acetate was distilled off under reduced pressure to yield Boc-Met-($^{13}$C-Ala)-OBzl.

6 N hydrogen chloride/dioxane (5 ml) was added to Boc-Met-($^{13}$C-Ala)-OBzl (1.40 g, equivalent to 3.23 mmol), and the resultant solution was agitated for 1 hr at room temperature. After concentration under reduced pressure, the residue was dissolved in DMF (8 ml). To this solution, benzoic acid (394 mg, 3.23 mmol) and HOBt (459 mg, 3.39 mmol) were added while ice-cooling and agitating. Then, WSCD (632 μl, 3.55 mmol) was added little by little, and the solution was agitated for 4 hr at room temperature. After addition of ethyl acetate, the reaction product was washed with saturated aqueous sodium hydrogencarbonate, water, 10% aqueous citric acid, and water in this order. The ethyl acetate was distilled off under reduced pressure. Hexane was added to the resultant residue, and the deposited solid was filtered out and dried under reduced pressure to yield Bz-Met-($^{13}$C-Ala)-OBzl.

To a mixture of Bz-Met-($^{13}$C-Ala)-OBzl (1.12 g, 2.69 mmol) and p-cresol (1.5 ml, 14 mmol), anhydrous hydrogen fluoride (8.5 ml) was introduced while cooling in a dry ice/methanol bath under agitating. Then, the solution was agitated for 1 hr under ice-cooling. After the hydrogen fluoride was distilled off under ice-cooling, diisopropyl ether was added to filter out the insoluble matter. The resultant solution was dried under reduced pressure to yield Bz-Met-($^{13}$C-Ala)-OH.

To Bz-Met-($^{13}$C-Ala)-OH in 5% aqueous acetonitrile (40 ml), 1 M aqueous sodium carbonate (1.47 ml, 1.47 mmol) was added to adjust the pH at 8. The trace insoluble matter was filtered off with a membrane filter. Then, the solution was purified by RP-HPLC (YMC-PAK ODS 10 μm, 30×250 mm, 1–60% MeCN, 80 min, 20 ml/min). The major fractions were collected and lyophilized to yield 546 mg of Bz-Met-($^{13}$C-Ala)-ONa.

Figure 5:
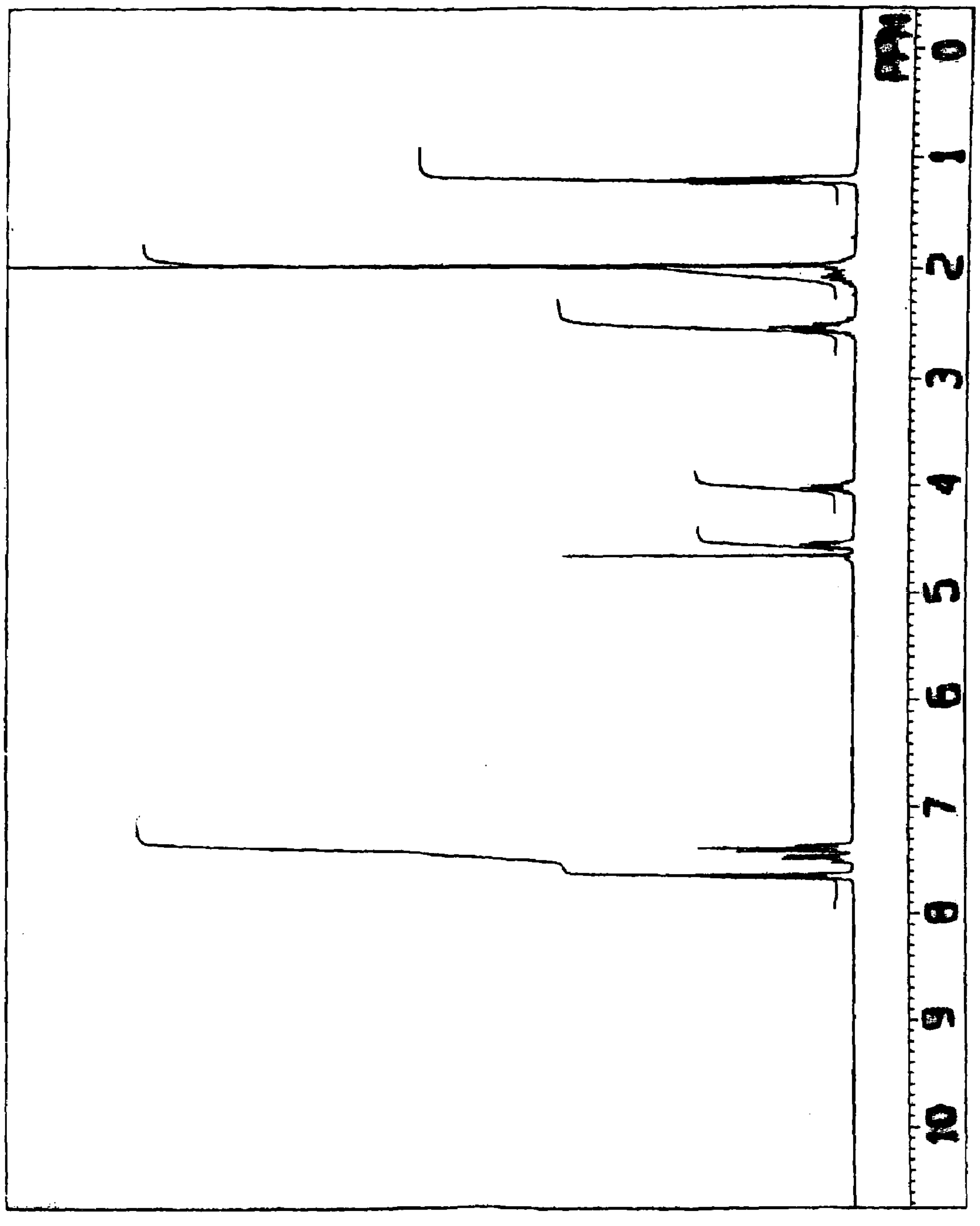
FIG. 5 shows the $^1H$-NMR spectrum (in $D_2O$) of Bz-Met-($^{13}C$-Ala)-ONa.

The confirmation of the structure of the resultant compound and the analysis of the $^{13}$C-labeled position were performed by $^1$H-NMR (FIG. 5), $^{13}$C-NMR and mass spectrometry.

$^{13}$C-NMR (in $D_2O$): 180.7 ppm

Mass spectrometry (ESI-MS): 348.1 (M+Na)

EXAMPLE 6

Preparation of N-benzoyl-L-seryl-$^{13}$C-L-alanine (Bz-Ser-($^{13}$C-Ala)) and its Sodium Salt HCl.H-($^{13}$C-Ala)-OBzl (700 mg, 3.23 mmol) obtained in the same manner as in Example 1, Boc-Ser(Bzl) (Peptide Institute Inc.) (954 mg, 3.23 mmol) and HOBt (459 mg, 3.39 mmol) were dissolved in DMF (8 ml). To this solution, WSCD (602 μl, 3.39 mmol) was added dropwise while ice-cooling and agitating, followed by agitation for 30 min under ice-cooling and for 3 hr at room temperature. After addition of ethyl acetate, the reaction product was washed with saturated aqueous sodium hydrogencarbonate, water, 10% aqueous citric acid, and water in this order and then dried over anhydrous sodium sulfate. The ethyl acetate was distilled off under reduced pressure to yield Boc-Ser(Bzl)-($^{13}$C-Ala)-OBzl.

6 N hydrogen chloride/dioxane (30 ml) was added to Boc-Ser(Bzl)-($^{13}$C-Ala)-OBzl (1.90 g, equivalent to 3.23 mmol), and the resultant solution was agitated for 1 hr at room temperature. After concentration under reduced pressure, the residue was dissolved in DMF (10 ml). To this solution, benzoic acid (253 mg, 3.23 mmol) and HOBt (279 mg, 3.23 mmol) were added while ice-cooling and agitating. Then, WSCD (602 μl, 3.39 mmol) was added little by little, and the solution was agitated for 30 min under ice-cooling and for 2 hr at room temperature. After addition of ethyl acetate, the reaction product was washed with saturated aqueous sodium hydrogencarbonate, water, 10% aqueous citric acid, and water in this order and then dried over anhydrous sodium sulfate. The ethyl acetate was distilled off under reduced pressure. Diethyl ether was added to the resultant residue, and the deposited solid was filtered out and dried under reduced pressure to yield Bz-Ser(Bzl)-($^{13}$C-Ala)-OBzl.

To a mixture of Bz-Ser(Bzl)-($^{13}$C-Ala)-OBzl (1.14 g, 2.47 mmol) and anisole (1.5 ml, 13.9 mmol), anhydrous hydrogen fluoride (8.5 ml) was introduced while cooling in a dry ice/methanol bath under agitating. Then, the solution was agitated for 1 hr under ice-cooling. After the hydrogen fluoride was distilled off under ice-cooling, water (20 ml) and diethyl ether (20 ml) were added to the resultant material and agitated. The resultant aqueous layer was lyophilized to yield Bz-Ser-($^{13}$C-Ala)-OH.

To an aqueous solution of Bz-Ser-($^{13}$C-Ala)-OH solution (20 ml), 1 M aqueous sodium carbonate (1.48 ml, 1.48 mmol) was added to adjust the pH at 8. The trace insoluble matter was filtered off with a membrane filter. Then, the solution was purified by RP-HPLC (YMC-PAK ODS 10 μm, 30×250 mm, 1–60% MeCN, 80 min, 20 ml/min). The major fractions were collected and lyophilized to yield 530 mg of Bz-Ser-($^{13}$C-Ala)-ONa.

Figure 6:
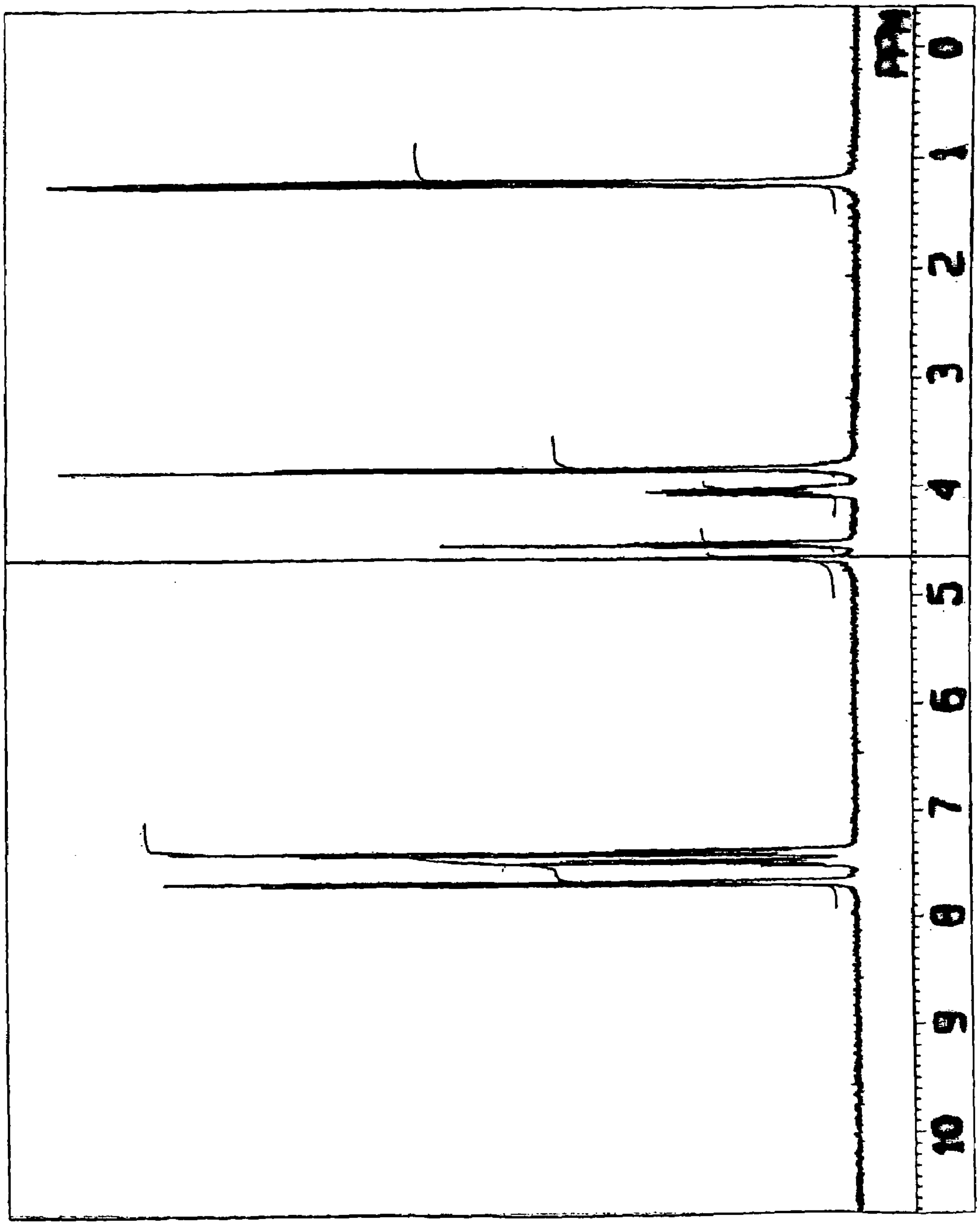
FIG. 6 shows the $^1H$-NMR spectrum (in $D_2O$) of Bz-Ser-($^{13}C$-Ala)-ONa.

The confirmation of the structure of the resultant compound and the analysis of the $^{13}$C-labeled position were performed by $^{1}$H-NMR (FIG. 6), $^{13}$C-NMR and mass spectrometry.

$^{13}$C-NMR (in $D_2O$): 180.9 ppm

Mass spectrometry (ESI-MS): 304.1 (M+Na)

EXAMPLE 7

Preparation of N-benzoyl-L-threonyl-$^{13}$C-L-alanine (Bz-Thr-($^{13}$C-Ala)) and its Sodium Salt HCl.H-($^{13}$C-Ala)-OBzl (700 mg, 3.23 mmol) obtained in the same manner as in Example 1, Boc-Thr(Bzl)(Peptide Institute Inc.) (999 mg, 3.23 mmol) and HOBt (459 mg, 3.39 mmol) were dissolved in DMF (8 ml). To this solution, WSCD (602 μl, 3.39 mmol) was added dropwise while ice-cooling and agitating, followed by agitation for 30 min under ice-cooling and for 1 hr at room temperature. After addition of ethyl acetate, the reaction product was washed with saturated aqueous sodium hydrogencarbonate, water, 10% aqueous citric acid, and water in this order and then dried over anhydrous sodium sulfate. The ethyl acetate was distilled off under reduced pressure, and the resultant crystalline residue was washed with hexane, filtered out, and dried under reduced pressure to yield Boc-Thr(Bzl)-($^{13}$C-Ala)-OBzl.

6 N hydrogen chloride/dioxane (30 ml) was added to Boc-Thr(Bzl)-($^{13}$C-Ala)-OBzl (1.38 g, 2.92 mmol), and the resultant solution was agitated for 1 hr at room temperature. After concentration under reduced pressure, the residue was dissolved in DMF (10 ml). To this solution, benzoic acid (356 mg, 2.92 mmol) and HOBt (415 mg, 3.07 mmol) were added while ice-cooling and agitating. Then, WSCD (574 μl, 3.07 mmol) was added little by little, and the solution was agitated for 30 min under ice-cooling and for 2 hr at room temperature. After addition of ethyl acetate, the reaction product was washed with saturated aqueous sodium hydrogencarbonate, water, 10% aqueous citric acid, and water in this order and then dried over anhydrous sodium sulfate. The ethyl acetate was distilled off under reduced pressure, and the resultant crystalline residue was washed with diethyl ether, filtered out and dried under reduced pressure to yield Bz-Thr(Bzl)-($^{13}$C-Ala)-OBzl.

To a mixture of Bz-Thr(Bzl)-($^{13}$C-Ala)-OBzl (779 mg, 1.64 mmol) and anisole (1.0 ml, 9.26 mmol), anhydrous hydrogen fluoride (9 ml) was introduced while cooling in a dry ice/methanol bath under agitating. Then, the solution was agitated for 1 hr under ice-cooling. After the hydrogen fluoride was distilled off under ice-cooling, water (20 ml) and diethyl ether (20 ml) were added to the resultant material and agitated. The resultant aqueous layer was lyophilized to yield Bz-Thr-($^{13}$C-Ala)-OH.

To an aqueous solution of Bz-Thr-($^{13}$C-Ala)-OH solution (20 ml), 1 M aqueous sodium carbonate (900 μl, 0.90 mmol) was added to adjust the pH at 8. The trace insoluble matter was filtered off with a membrane filter. Then, the solution was purified by RP-HPLC (YMC-PAK ODS 10 μm, 30×250 mm, 1–60% MeCN, 80 min, 20 ml/min). The major fractions were collected and lyophilized to yield 353 mg of Bz-Thr-($^{13}$C-Ala)-ONa.

Figure 7:
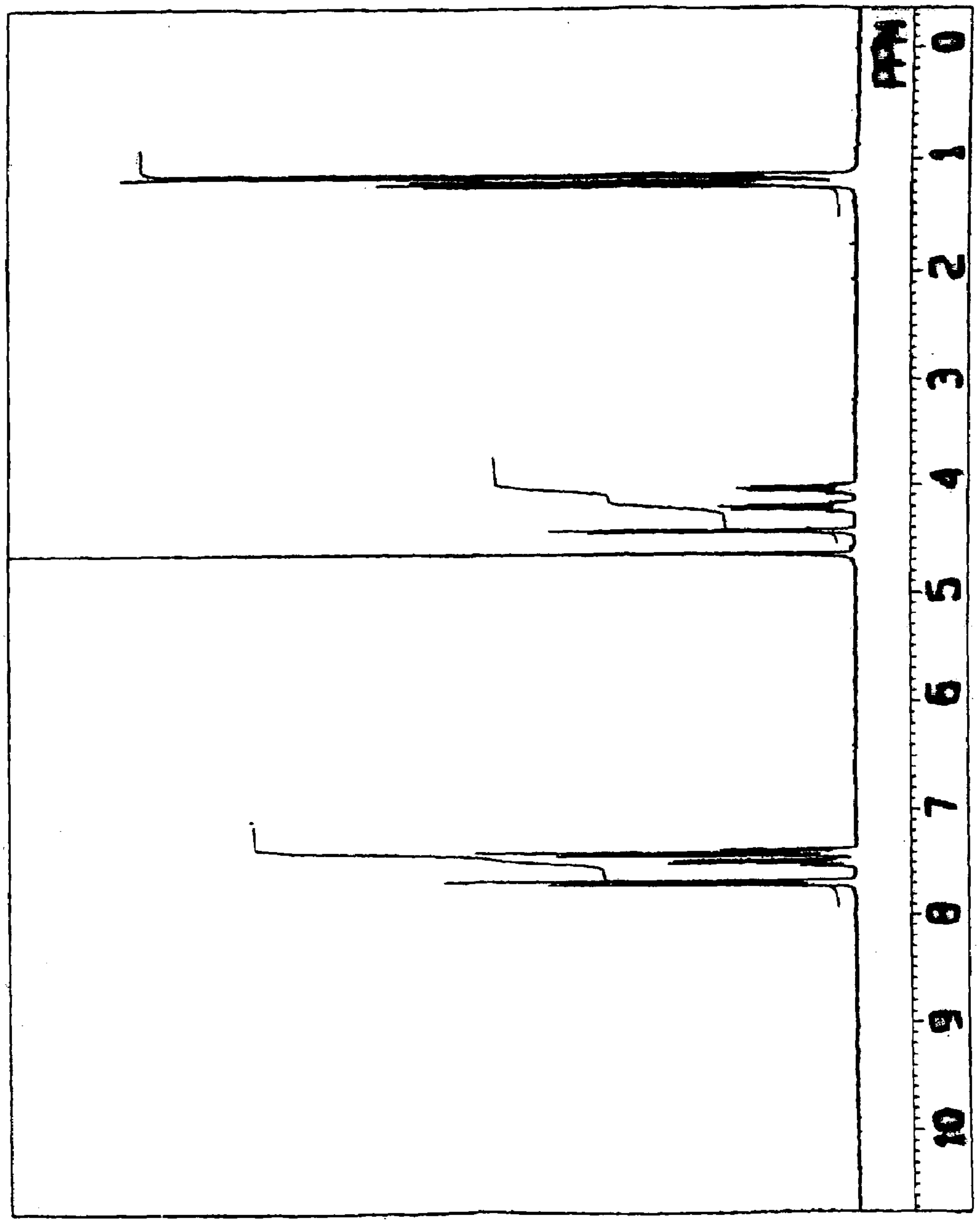
FIG. 7 shows the $^1H$-NMR spectrum (in $D_2O$) of Bz-Thr-($^{13}C$-Ala)-ONa.

The confirmation of the structure of the resultant compound and the analysis of the $^{13}$C-labeled position were performed by $^{1}$H-NMR (FIG. 7), $^{13}$C-NMR and mass spectrometry.

$^{13}$C-NMR (in $D_2O$): 180.8 ppm

Mass spectrometry (ESI-MS): 318.1 (M+Na)

EXAMPLE 8

Preparation of benzyloxycarbonyl-L-methionyl-$^{13}$C-L-alanine (Z-Met-($^{13}$C-Ala)) and its Sodium Salt HCl.H-($^{13}$C-Ala)-OBzl (6.50 g, 30.0 mmol) obtained in the same manner as in Example 1, Z-Met (Peptide Institute Inc.) (8.50 g, 30.0 mmol) and HOBt (4.26 g, 31.5 mmol) were dissolved in DMF (60 ml). To this solution, WSCD (5.58 ml, 31.5 mmol) was added dropwise while ice-cooling and agitating, followed by agitation overnight at room temperature. After concentration under reduced pressure, ethyl acetate was added thereto. The resultant reaction product was washed with water, saturated aqueous sodium hydrogencarbonate, water, 10% aqueous citric acid, and water in this order, and then dried over anhydrous magnesium sulfate. The ethyl acetate was distilled off under reduced pressure, and the resultant residue was washed with diisopropyl ether and filtered out to yield Z-Met-($^{13}$C-Ala)-OBzl.

To a suspension of Z-Met-($^{13}$C-Ala)-OBzl (13.13 g, 29.5 mmol) in methanol (90 ml), 2 N aqueous sodium hydroxide (29.5 ml, 58.9 mmol) was added and agitated for 1 hr at room temperature. The methanol was distilled off under reduced pressure, and concentrated hydrochloric acid was added to the solution to adjust the pH at 1. Then, the solution was extracted with ethyl acetate twice, washed with saturated aqueous sodium chloride, and dried over magnesium sulfate. After concentration under reduced pressure, the residue was solidified with hexane/diisopropyl ether. The resultant colorless solid was filtered out, re-dissolved in ethyl acetate and washed with ultra-pure water. After concentration under reduced pressure, the residue was washed with hexane and dried under reduced pressure to yield Z-Met-($^{13}$C-Ala)-OH.

To Z-Met-($^{13}$C-Ala)-OH (10.07 g, 28.3 mmol) in 30% acetonitrile (50 ml), sodium hydrogencarbonate (2.38 g, 28.3 mmol) was added and dissolved. The resultant solution was diluted with water (100 ml) and then lyophilized to yield 10.72 g of Z-Met-($^{13}$C-Ala)-ONa.

Figure 8:
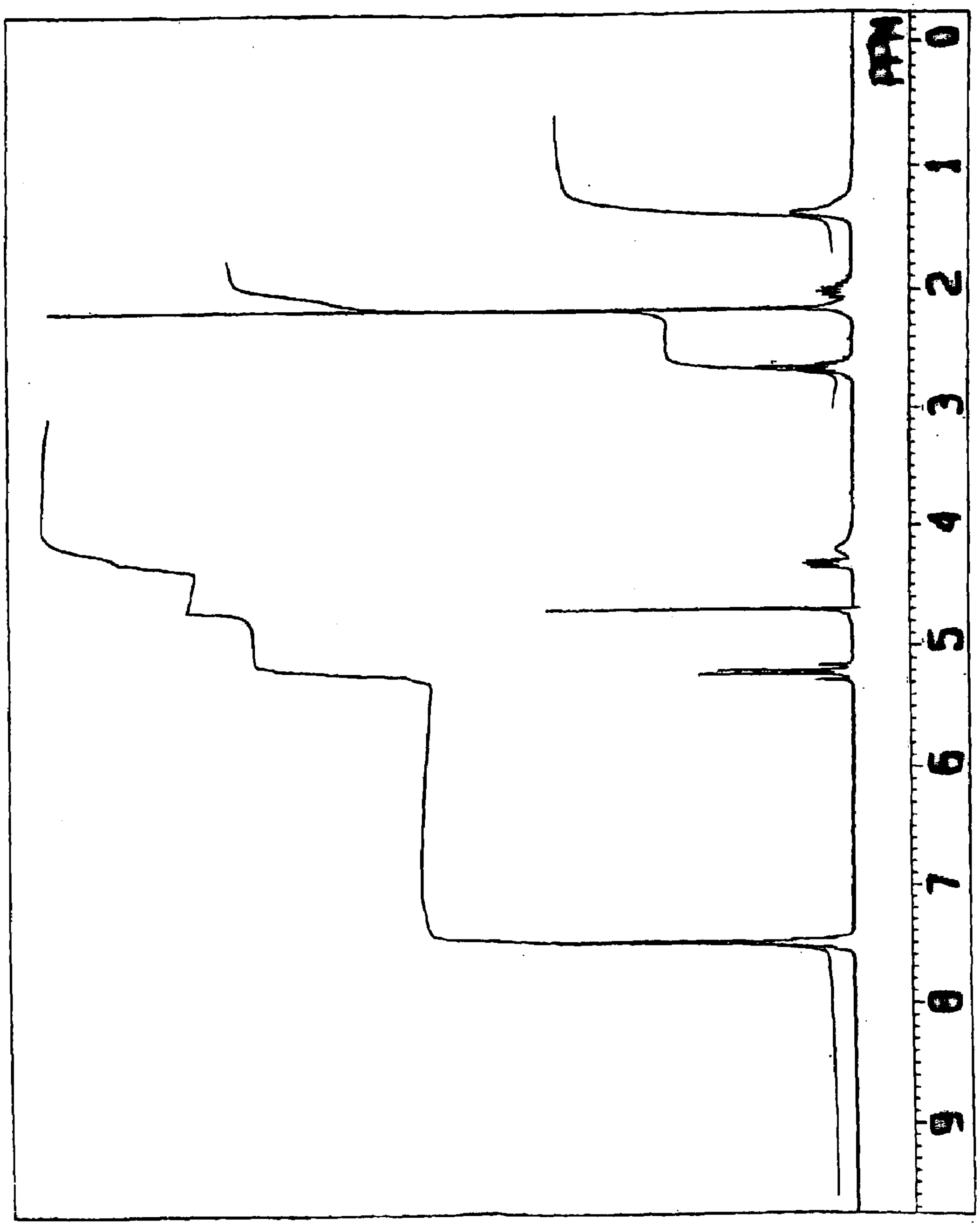
FIG. 8 shows the $^1H$-NMR spectrum (in $D_2O$) of Z-Met-($^{13}C$-Ala)-ONa.

The confirmation of the structure of the resultant compound and the analysis of the $^{13}$C-labeled position were performed by $^{1}$H-NMR (FIG. 8), $^{13}$C-NMR and mass spectrometry.

$^{13}$C-NMR (in $D_2O$): 180.7 ppm

Mass spectrometry (ESI-MS): 378.1 (M+Na)

EXAMPLE 9

Preparation of t-butyloxycarbonyl-L-methionyl-$^{13}$C-L-alanine (Boc-Met-($^{13}$C-Ala)) and its Sodium Salt HCl.H-($^{13}$C-Ala)-OBzl (27.4 g, 110 mmol) obtained in the same manner as in Example 1, Boc-Met (Peptide Institute Inc.) (27.4 g, 110 mmol) and HOBt (15.6 g, 115 mmol) were dissolved in DMF (200 ml). To this solution, WSCD (21.0 ml, 115 mmol) was added dropwise while ice-cooling and agitating, followed by agitation for 2 hr at room temperature. Then, ethyl acetate (500 ml) was added thereto, and the resultant reaction product was washed with water, saturated aqueous sodium hydrogencarbonate, water, 10% aqueous citric acid, and water in this order, and dried over anhydrous sodium sulfate. Distilling off the ethyl acetate under reduced pressure resulted in a colorless, oily material. This material was dried under reduced pressure to yield Boc-Met-($^{13}$C-Ala)-OBzl.

Boc-Met-($^{13}$C-Ala)-OBzl (12.9 g, 31.3 mmol) was suspended in 50% methanol (100 ml). 1 N sodium hydroxide (47.0 ml, 47.0 mmol) was added thereto under ice-cooling, and agitated for 30 min at room temperature. The methanol was distilled off under reduced pressure. Then, water was added to the resultant residue, which was then washed with diethyl ether twice. 6 N hydrochloric acid was added thereto to adjust the pH at 1. Then, the solution was extracted with ethyl acetate twice. The organic layer was combined, and the mixture was washed with 1 N hydrochloric acid, water, and saturated aqueous sodium chloride in this order, and then dried over anhydrous sodium sulfate. After concentration under reduced pressure, the residue was washed with hexane. In order to remove trace impurities, the residue was dissolved in 150 ml of methanol, and 5 g of active carbon was added thereto, followed by filtration. After concentration under reduced pressure, the residue was dissolved in 20% acetonitrile and lyophilized to yield Boc-Met-($^{13}$C-Ala)-OH.0.1$H_2O$.

To Boc-Met-($^{13}$C-Ala)-OH.0.1$H_2O$ (5.96 g, 18.4 mmol) in 10% aqueous acetonitrile (100 ml), sodium hydrogencarbonate (1.55 g, 18.4 mmol) was added and dissolved. After removal of the trace insoluble matter with a membrane filter, the solution was lyophilized to yield 6.28 g of Boc-Met-($^{13}$C-Ala)-ONa.

Figure 9:
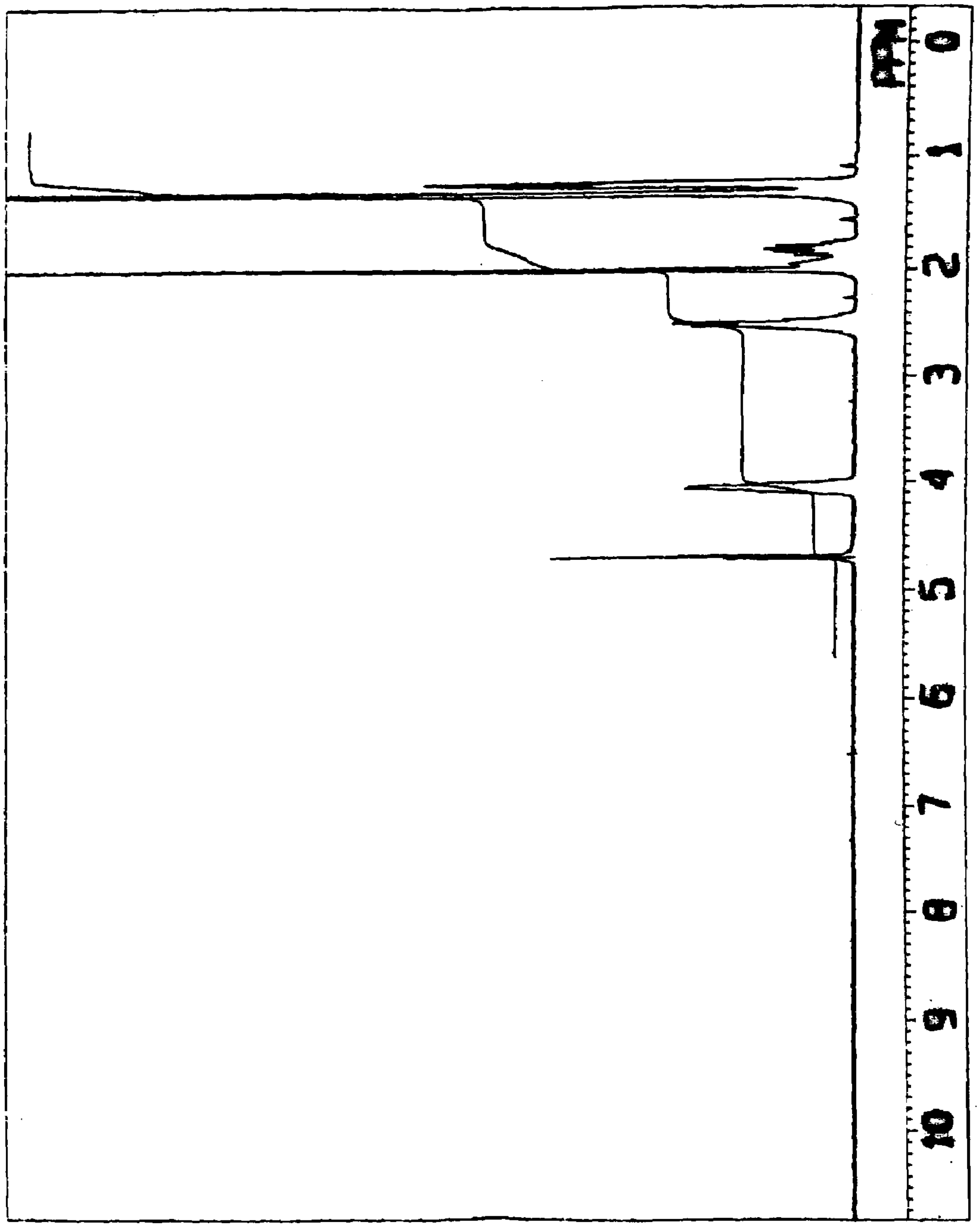
FIG. 9 shows the $^1H$-NMR spectrum (in $D_2O$) of Boc-Met-($^{13}C$-Ala)-ONa.

The confirmation of the structure of the resultant compound and the analysis of the $^{13}$C-labeled position were performed by $^{1}$H-NMR (FIG. 9), $^{13}$C-NMR and mass spectrometry.

$^{13}$C-NMR (in $D_2O$): 180.7 ppm

Mass spectrometry (ESI-MS): 344.1 (M+Na)

EXAMPLE 10

Preparation of acetyl-L-methionyl-$^{13}$C-L-alanine (Ac-Met-($^{13}$C-Ala)) and its Sodium Salt To Boc-Met-($^{13}$C-Ala)-OBzl (17.6 g, 42.8 mmol) obtained in the same manner as in Example 9, 4.5 N HCl/dioxane (95 ml, 0.428 mol) was added under ice-cooling, followed by agitation for 60 min at room temperature. The dioxane was distilled off under reduced pressure, and diethyl ether was added to the residue for washing. Then, the supernatant was discarded, and the remaining oily material was solidified with hexane. The resultant solid was filtered out, washed with hexane, and dissolved in DMF (150 ml). Triethylamine (9.00 ml, 62.3 mmol) and acetic anhydride (4.4 ml, 46.8 mol) were added dropwise to the solution under ice-cooling, which was then agitated for 1 hr at room temperature. After addition of ethyl acetate, the reaction product was washed with water and saturated aqueous sodium chloride in this order, and dried over anhydrous sodium sulfate. The solvent was distilled off under reduced pressure, and diethyl ether was added to the residue for washing. Then, the residue was filtered out and dried under reduced pressure to yield Ac-Met-($^{13}$C-Ala)-OBzl.

To a suspension of Ac-Met-($^{13}$C-Ala)-OBzl (9.64 g, 27.3 mmol) in 50% methanol (200 ml), 1 N aqueous sodium hydroxide (40.9 ml, 40.9 mmol) was added under ice-cooling, and agitated for 1.5 hr at room temperature. The methanol was distilled off under reduced pressure. Then, water was added to the resultant residue, which was then washed with diethyl ether twice. 6 N hydrochloric acid was added to the aqueous layer to adjust the pH at 1, followed by extraction with chloroform. However, no extract was obtained. Then, sodium hydrogencarbonate was added to the solution to adjust the pH at 5, and the solution was left overnight. After adjustment of the pH at 2 with TFA, major fractions were collected by RP-HPLC (1-1–60% aq. MeCN (0–10–60 min)) and lyophilized to yield Ac-Met-($^{13}$C-Ala)-OH.

To Ac-Met-($^{13}$C-Ala)-OH (6.00 g, 22.8 mmol) in 10% aqueous acetonitrile (100 ml), sodium hydrogencarbonate (1.91 g, 22.8 mmol) was added and dissolved. After removal of the trace insoluble matter with a membrane filter, the solution was lyophilized. The resultant oily material was dissolved in water (150 ml) and lyophilized again to yield 6.24 g of Ac-Met-($^{13}$C-Ala)-ONa.

Figure 10:
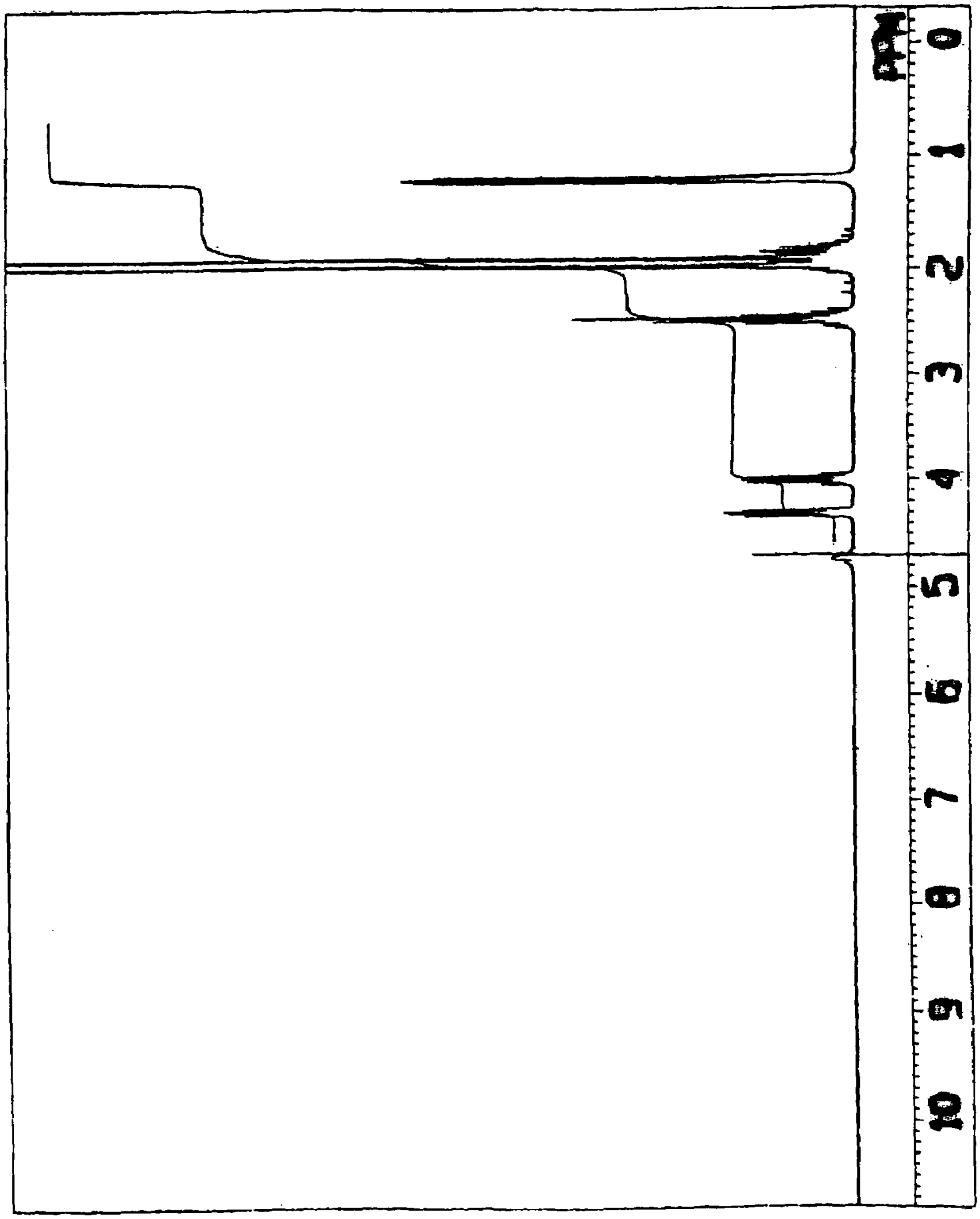
FIG. 10 shows the $^1H$-NMR spectrum (in $D_2O$) of Ac-Met-($^{13}C$-Ala)-ONa.

The confirmation of the structure of the resultant compound and the analysis of the $^{13}$C-labeled position were performed by $^{1}$H-NMR (FIG. 10), $^{13}$C-NMR and mass spectrometry.

$^{13}$C-NMR (in $D_2O$): 180.7 ppm

Mass spectrometry (ESI-MS): 286.1 (M+Na)

EXAMPLE 11

Preparation of t-butyloxycarbonyl-L-phenylalanyl-$^{13}$C-L-alanine (Boc-L-Phe-($^{13}$C-Ala)) and its Sodium Salt HCl.H-($^{13}$C-Ala)-OBzl (20.8 g, 96.0 mmol) obtained in the same manner as in Example 1, Boc-Phe (Peptide Institute Inc.) (25.5 g, 96.0 mmol) and HOBt (13.6 g, 101 mmol) were dissolved in DMF (200 ml). To this solution, WSCD (18.4 ml, 101 mmol) was added dropwise while ice-cooling and agitating, followed by agitation for 3 hr at room temperature. Then, ethyl acetate was added thereto, and the resultant reaction product was washed with water, saturated aqueous sodium hydrogencarbonate, water, 10% aqueous citric acid, and water in this order, and dried over anhydrous sodium sulfate. The ethyl acetate was distilled off under reduced pressure, followed by crystallization with hexane and filtering-out of the crystals. After washing with hexane, the crystals were dried under reduced pressure to yield Boc-Phe-($^{13}$C-Ala)-OBzl.

Boc-Phe-($^{13}$C-Ala)-OBzl (9.40 g, 22.0 mmol) was dissolved in acetic acid (100 ml), and 5% palladium-carbon (2 g) was added thereto. Hydrogen gas was blown thereinto for 120 min while agitating at room temperature. The catalyst was filtered off, and the acetic acid was distilled off. The residue was dissolved in ethyl acetate, washed with saturated aqueous sodium chloride and dried over magnesium sulfate. After concentration under reduced pressure, the residue was washed with hexane and filtered out to yield Boc-Phe-($^{13}$C-Ala)-OH.0.15Hexane 0.24$H_2O$.

To Boc-Phe-($^{13}$C-Ala)-OH.0.15Hexane.0.24$H_2O$ (7.35 g, 20.7 mmol) in 50% aqueous acetonitrile (80 ml), sodium hydrogencarbonate (1.74 g, 20.7 mmol) was added and dissolved. After addition of water (100 ml), the trace insoluble matter was filtered off with a membrane filter. Then, the solution was lyophilized to yield 7.10 g of Boc-Phe-($^{13}$C-Ala)-ONa.

Figure 11:
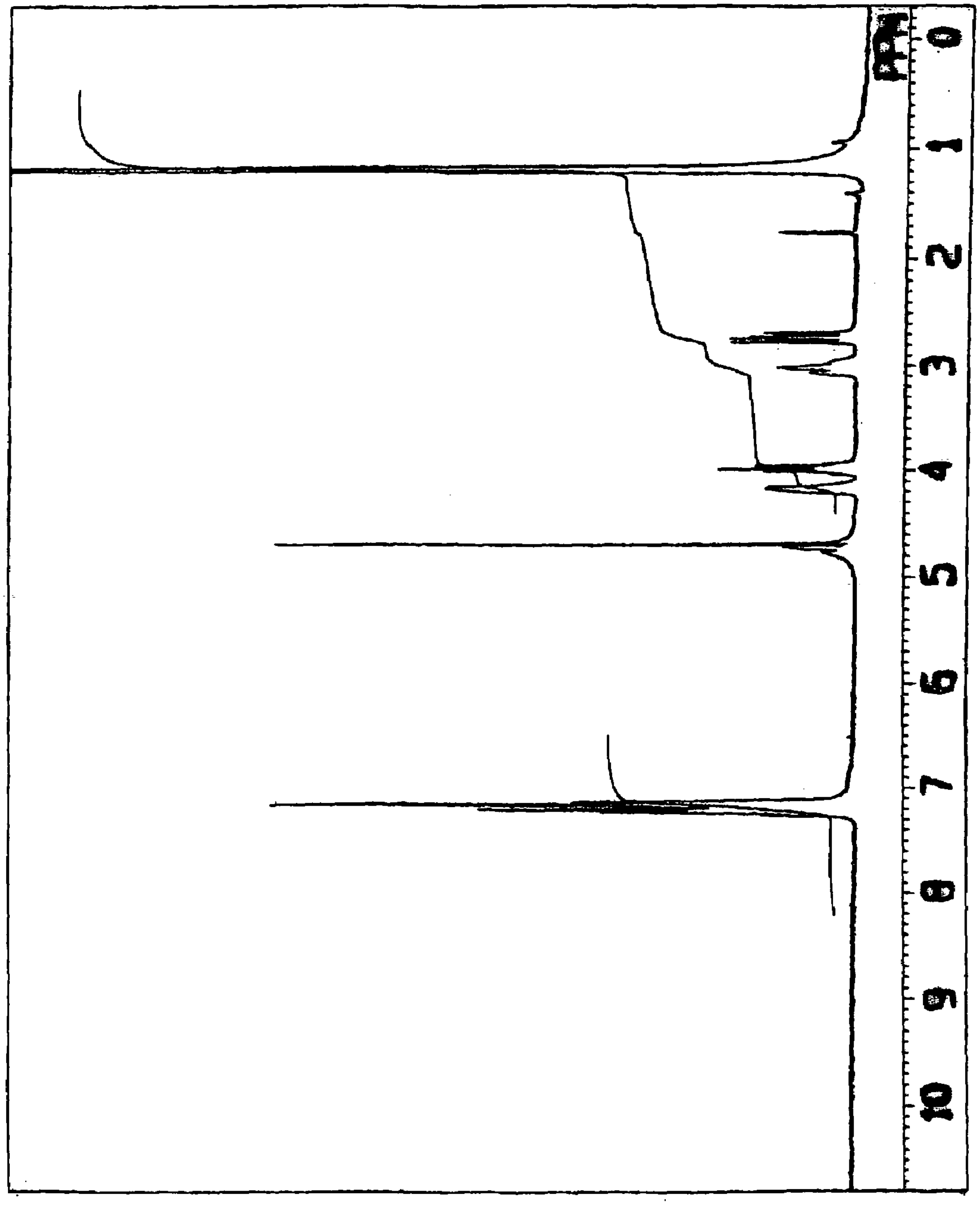
FIG. 11 shows the $^1H$-NMR spectrum (in $D_2O$ ) of Boc-Phe-($^{13}C$-Ala)-ONa.

The confirmation of the structure of the resultant compound and the analysis of the $^{13}$C-labeled position were performed by $^{1}$H-NMR (FIG. 11), $^{13}$C-NMR and mass spectrometry.

$^{13}$C-NMR (in $D_2O$): 181.7 ppm

Mass spectrometry (ESI-MS): 360.3 (M+Na)

EXAMPLE 12

Bz-amino acid-($^{13}$C-Ala) Breath Test 12-1 Method

Overnight-fasted rats (male, Wistar, 8-week old) in the awake state were individually fixed in a rat holder of a microwave irradiation apparatus. The breath was collected at a rate of about 100 to 300 ml/min using a stroke pump (Variable Stroke Pump VS-500; Shibata Kagaku Kogyo), and the $CO_2$ concentration therein was maintained at about 3%. A Perma Pure drier (MD-050-12P; Perma Pure INC.) was set between the rat holder and the stroke pump to remove water vapor from the breath. When the $CO_2$ concentration was stabilized, the rat was temporarily released from the rat holder. A $^{13}$C-labeled dipeptide or a sodium salt thereof each dissolved in distilled water was administered to the stomach of the rat using an oral probe [dose: 35 μmol/kg (5 ml/kg)]. The breath was sampled with a syringe every 5 min until up to 20 min. A 15 ml sample was transferred from the syringe into a vacuum vial (10 ml), sealed and subjected to automated analysis by GC-MS (Breath MAT) [Finnigan-MAT]. $\Delta^{13}$C(‰) was calculated from $\delta^{13}$C values which are $^{13}$C values of a sample (i.e. differences from the standard substance PDB) using the following formula.

$$\Delta^{13}C(‰)=(\delta^{13}C)t\,min-(\delta^{13}C)0\ min$$

<Breath MAT Measuring Conditions>

Apparatus: Breath MAT plus (Finningan)

Carrier gas: He

Measured ions: m/z=44, 45, 46

While 19 $^{13}$C-labeled dipeptides and sodium salts of $^{13}$C-labeled dipeptides were used in the breath test, Bz-Phe-($^{13}$C-Ala)-ONa, Bz-Gln-($^{13}$C-Ala)-ONa, Bz-Val-($^{13}$C-Ala)-ONa, Bz-Tyr-($^{13}$C-Ala)-ONa, Bz-Met-($^{13}$C-Ala)-ONa, Bz-Ser-($^{13}$C-Ala)-ONa and Bz-Thr-($^{13}$C-Ala)-ONa were prepared in Examples 1 to 7, respectively; Bz-Ala-($^{13}$C-Ala)-ONa was prepared by the methods described in Examples 4 and 5 in Japanese Unexamined Patent Publication No. 2000-053697; Bz-Arg-($^{13}$C-Ala), Bz-Leu-($^{13}$C-Ala)-ONa, Bz-Asn-($^{13}$C-Ala)-ONa, Bz-Ile-($^{13}$C-Ala)-ONa, Bz-Trp-($^{13}$C-Ala)-ONa, Bz-Lys-($^{13}$C-Ala), Bz-His-($^{13}$C-Ala)-ONa, Bz-Gly-($^{13}$C-Ala)-ONa, Bz-Cys-($^{13}$C-Ala)-ONa, the sodium salt of Bz-Glu-($^{13}$C-Ala) and the sodium salt of Bz-Asp-($^{13}$C-Ala) were prepared by methods based on those described in Examples 4 and 5 in Japanese Unexamined Patent Publication No. 2000-053697.

12-2 Results $^{13}$C-dipeptide breath tests were carried out using dipeptides having a structure of Bz-amino acid-($^{13}$C-Ala) and sodium salts thereof [dose: 35 μmol/kg (5 ml/kg)] and peak values in the time course of $\Delta^{13}$C(‰) values (hereinafter, referred to as "$^{13}$C(‰) peak value(s)") were compared. As shown in Table 1, the $\Delta^{13}$C(‰) peak values in the breath tests with Bz-Phe-($^{13}$C-Ala)-ONa, Bz-Gln-($^{13}$C-Ala)-ONa, Bz-Val-($^{13}$C-Ala)-ONa, Bz-Tyr-($^{13}$C-Ala)-ONa, Bz-Met-($^{13}$C-Ala)-ONa, Bz-Ser-($^{13}$C-Ala)-ONa and Bz-Thr-($^{13}$C-Ala)-ONa were higher than the $\Delta^{13}$C(‰) peak value of Bz-Ala-($^{13}$C-Ala)-ONa that showed a higher $\Delta^{13}$C(‰) value in $^{13}$C-peptide breath test than any other peptides described in Japanese Unexamined Patent Publication No. 2000-053697.

TABLE 1

| $^{13}$C-dipeptide | Peak time (min) | $\Delta^{13}$C(‰) peak value |
|---|---|---|
| Na salt of Bz-Phe-($^{13}$C-Ala) | 10 | 55.62 |
| Na salt of Bz-Gln-($^{13}$C-Ala) | 10 | 54.56 |
| Na salt of Bz-Val-($^{13}$C-Ala) | 15 | 52.89 |
| Na salt of Bz-Tyr-($^{13}$C-Ala) | 15 | 52.64 |
| Na salt of Bz-Met-($^{13}$C-Ala) | 10 | 48.88 |
| Na salt of Bz-Ser-($^{13}$C-Ala) | 15 | 47.48 |
| Na salt of Bz-Thr-($^{13}$C-Ala) | 10 | 47.36 |
| Na salt of Bz-Ala-($^{13}$C-Ala) | 10 | 45.88 |
| Bz-Arg-($^{13}$C-Ala) | 15 | 42.83 |
| Na salt of Bz-Leu-($^{13}$C-Ala) | 15 | 42.77 |
| Na salt of Bz-Asn-($^{13}$C-Ala) | 15 | 41.74 |
| Na salt of Bz-Ile-($^{13}$C-Ala) | 20 | 39.82 |
| Na salt of Bz-Trp-($^{13}$C-Ala) | 15 | 39.76 |
| Bz-Lys-($^{13}$C-Ala) | 15 | 38.57 |
| Na salt of Bz-His-($^{13}$C-Ala) | 20 | 36.17 |
| Na salt of Bz-Gly-($^{13}$C-Ala) | 20 | 32.14 |
| Na salt of Bz-Cys-($^{13}$C-Ala) | 10 | 31.52 |
| Na salt of Bz-Glu-($^{13}$C-Ala) | 20 | 29.00 |
| Na salt of Bz-Asp-($^{13}$C-Ala) | 20 | 11.47 |

EXAMPLE 13

Breath Test With Ac-Met-($^{13}$C-Ala)-ONa, Z-Met-($^{13}$C-Ala)-ONa, Boc-Met-($^{13}$C-Ala)-ONa or Boc-Phe-($^{13}$C-Ala)-ONa Using Ac-Met-($^{13}$C-Ala)-ONa, Z-Met-($^{13}$C-Ala)-ONa, Boc-Met-($^{13}$C-Ala)-ONa or Boc-Phe-($^{13}$C-Ala)-ONa [dose: 35 μmol/kg (5 ml/kg)], $^{13}$C-breath tests were carried out in the same manner as in Example 12. The resultant $\Delta^{13}$C(‰) peak values were compared with the $\Delta^{13}$C(‰) peak value in the Bz-Ala-($^{13}$C-Ala)-ONa breath test. As shown in Table 2, the $\Delta^{13}$C(‰) peak values in the breath tests with Ac-Met- ($^{13}$C-Ala)-ONa, Z-Met-($^{13}$C-Ala)-ONa, Boc-Met-($^{13}$C-Ala)-ONa and Boc-Phe-($^{13}$C-Ala)-ONa were higher than the $\Delta^{13}$C(‰) peak value in the Bz-Ala-($^{13}$C-Ala)-ONa breath test.

TABLE 2

| $^{13}$C-dipeptide | Peak time (min) | $\Delta^{13}$C(‰) peak value |
|---|---|---|
| Na salt of Ac-Met-($^{13}$C-Ala) | 15 | 63.15 |
| Na salt of Boc-Met-($^{13}$C-Ala) | 15 | 55.50 |
| Na salt of Z-Met-($^{13}$C-Ala) | 15 | 48.71 |
| Na salt of Boc-Phe-($^{13}$C-Ala) | 20 | 46.06 |
| Na salt of Bz-Ala-($^{13}$C-Ala) | 10 | 45.88 |

The Ac-Met-($^{13}$C-Ala)-ONa, Z-Met-($^{13}$C-Ala)-ONa, Boc-Met-($^{13}$C-Ala)-ONa and Boc-Phe-($^{13}$C-Ala)-ONa were prepared in Examples 8 to 11, respectively; the Bz-Ala-($^{13}$C-Ala)-ONa was prepared by the methods described in Examples 4 and 5 in Japanese Unexamined Patent Publication No. 2000-053697.

EXAMPLE 14

Breath Test With Bz-Phe-($^{13}$C-Ala)-ONa, Bz-Gln-($^{13}$C-Ala)-ONa, Bz-Val-($^{13}$C-Ala)-ONa, Bz-Tyr-($^{13}$C-Ala)-ONa, Bz-Met-($^{13}$C-Ala)-ONa, Bz-Ser-($^{13}$C-Ala)-ONa, Bz-Thr-($^{13}$C-Ala)-ONa or Boc-Phe-($^{13}$C-Ala)-ONa 14-1 Creation of Chronic Pancreatitis Rats Chronic pancreatitis rats were created according to the method of Mundlos et al., Pancreas 1:29 (1986). Oleic acid was injected into the pancreatic duct of 5-week old Wistar male rats. After breeding for 3 weeks, they were used in $^{13}$C-dipeptide breath tests.

14-2 Method of the Breath Test

As in Example 12, Bz-Phe-($^{13}$C-Ala)-ONa [dose: 12.6 mg/kg (35 μmol/kg)], BZ-Gln-($^{13}$C-Ala)-ONa [dose: 12.0 mg/kg (35 μmol/kg)], Bz-Val-($^{13}$C-Ala)-ONa [dose: 11.0 mg/kg (35 μmol/kg)], Bz-Tyr-($^{13}$C-Ala)-ONa [dose: 13.2 mg/kg (35 μmol/kg)], Bz-Met-($^{13}$C-Ala)-ONa [dose: 12.1 mg/kg (35 μmol/kg)], Bz-Ser-($^{13}$C-Ala)-ONa [dose: 10.6 mg/kg (35 μmol/kg)], Bz-Thr-($^{13}$C-Ala)-ONa [dose: 11.0 mg/kg (35 μmol/kg)] or Boc-Phe-($^{13}$C-Ala)-ONa [dose: 8.84 mg/kg (24.6 μmol/kg)] was administered orally to normal rats and chronic pancreatitis rats. Then, the time course of the degree of increase of the $^{13}$C concentration in exhaled $CO_2$ ($\Delta^{13}$C(‰)) was measured.

Bz-Phe-($^{13}$C-Ala)-ONa, Bz-Gln-($^{13}$C-Ala)-ONa, Bz-Val-($^{13}$C-Ala)-ONa, Bz-Tyr-($^{13}$C-Ala)-ONa, Bz-Met-($^{13}$C-Ala)-ONa, Bz-Ser-($^{13}$C-Ala)-ONa and Bz-Thr-($^{13}$C-Ala)-ONa were prepared in Examples 1 to 7, respectively; Boc-Phe-($^{13}$C-Ala)-ONa was prepared in Example 11.

14-3 Results of the Breath Test

Figure 12:
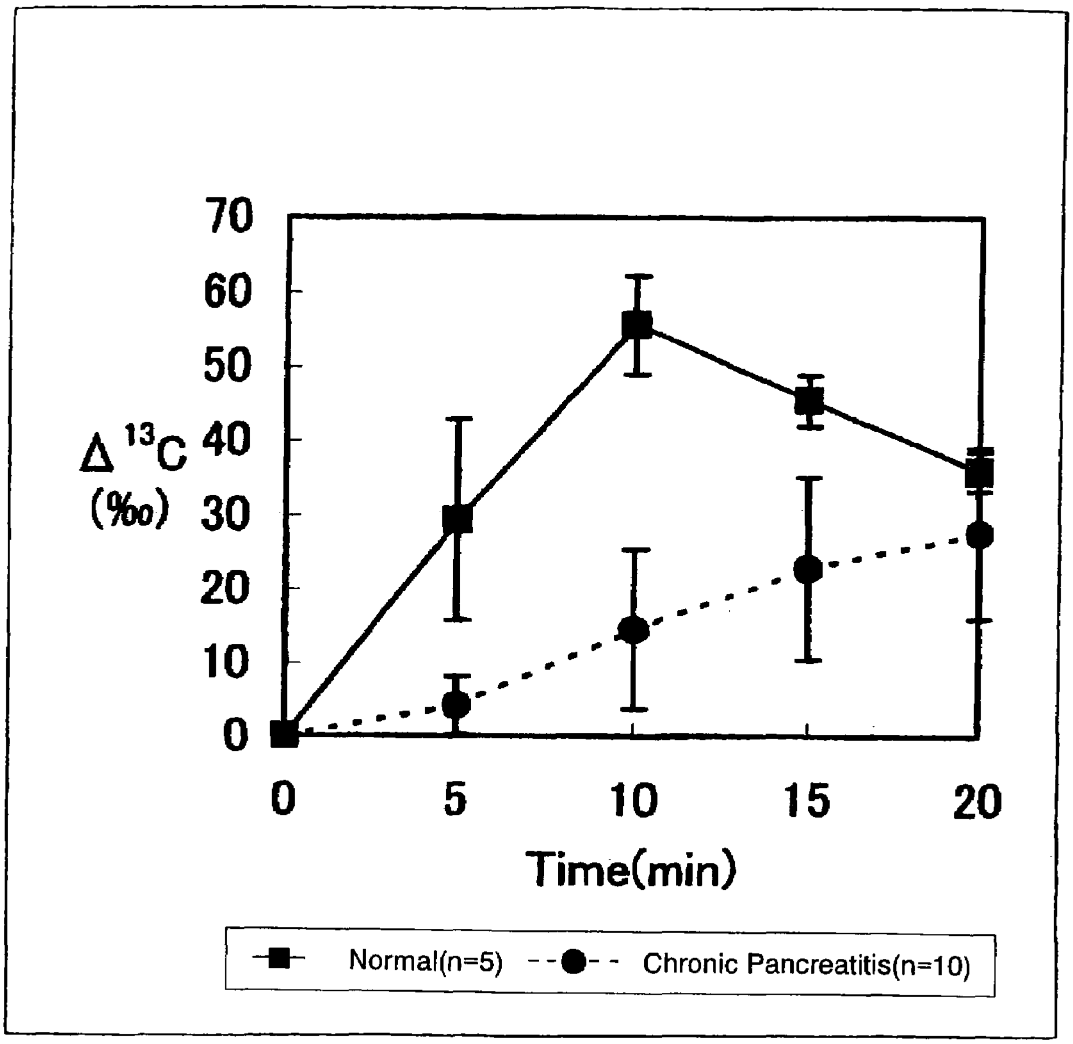
FIG. 12 shows the time course of the degree of increase of $^{13}C$ concentration in exhaled $CO_2$ ($\Delta^{13}C$(‰)) after administration of Bz-Phe-($^{13}C$-Ala)-ONa. At 0 min, Bz-Phe-($^{13}C$-Ala)-ONa was administered orally to chronic pancreatitis rats (●, n=10) and normal rats (■, n=5) at 12.6 mg/kg. The error bars represent SD.

The results of Bz-Phe-($^{13}$C-Ala)-ONa breath test were as follows. The $\Delta^{13}$C (‰) value at 5 min after the administration was 4.17±3.95 in the chronic pancreatitis rats, whereas the value was 29.32±13.57 in the normal rats; the value was very significantly smaller in the chronic pancreatitis rats ($p<0.001$). The $\Delta^{13}$C(‰) value at 10 min after the administration was 14.56±10.79 in the chronic pancreatitis rats, whereas the value was 55.62±6.62 in the normal rats; the value was very significantly smaller in the chronic pancreatitis rats ($p<0.0001$). The $\Delta^{13}$C(‰) value at 15 min after the administration was 22.80±12.36 in the chronic pancreatitis rats, whereas the value was 45.44±3.44 in the normal rats; the value was significantly smaller in the chronic pancreatitis rats ($p<0.01$). (See FIG. 12.)

Figure 13:
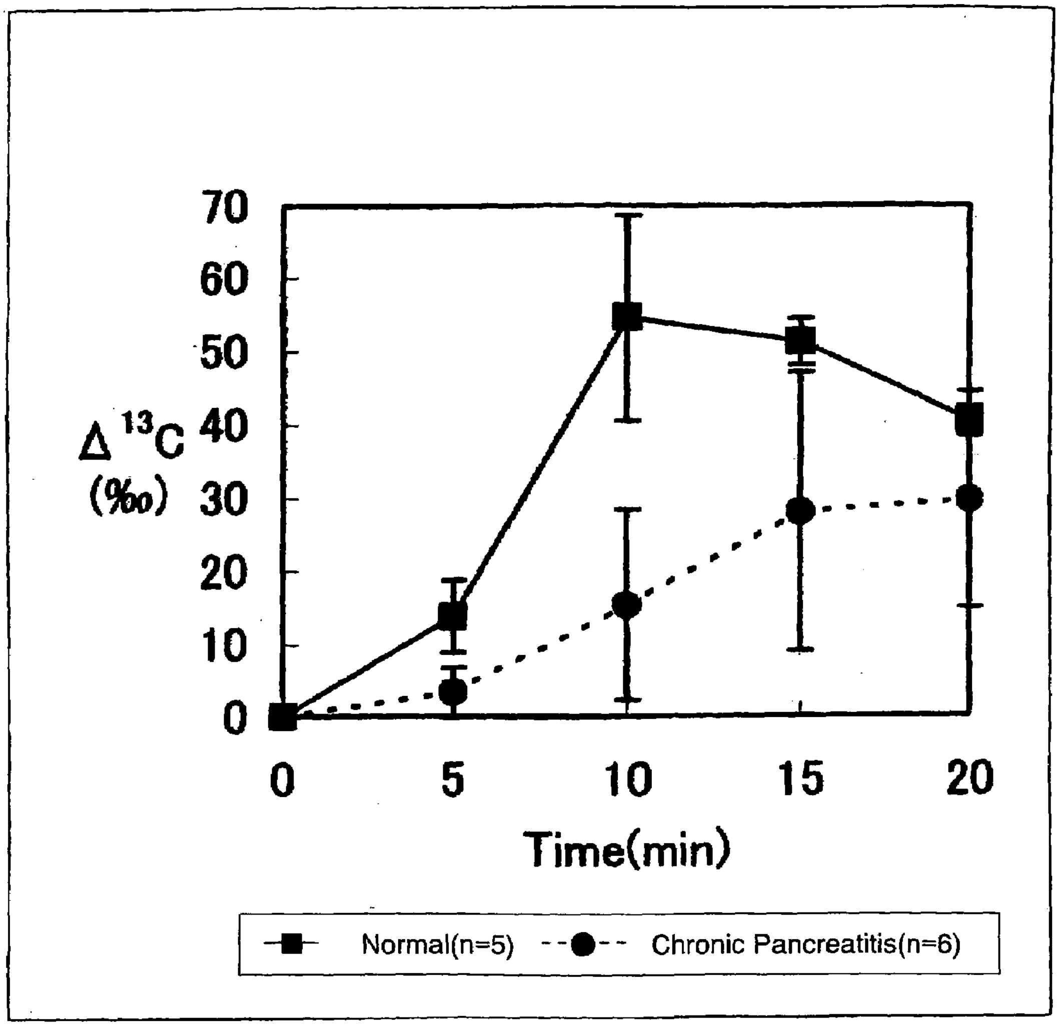
FIG. 13 shows the time course of the degree of increase of $^{13}C$ concentration in exhaled $CO_2$ ($\Delta^{13}C$(‰)) after administration of Bz-Gln-($^{13}C$-Ala)-ONa. At 0 min, Bz-Gln-($^{13}C$-Ala)-ONa was administered orally to chronic pancreatitis rats (●, n=6) and normal rats (■, n=5) at 12.0 mg/kg. The error bars represent SD.

The results of Bz-Gln-($^{13}$C-Ala)-ONa breath test were as follows. The $\Delta^{13}$C(‰) value at 5 min after the administration was 3.41±3.44 in the chronic pancreatitis rats, whereas the value was 13.86±4.98 in the normal rats; the value was significantly smaller in the chronic pancreatitis rats ($p<0.01$). The $\Delta^{13}$C(‰) value at 10 min after the administration was 15.32±13.04 in the chronic pancreatitis rats, whereas the value was 54.56±14.10 in the normal rats; the value was significantly smaller in the chronic pancreatitis rats ($p<0.01$). The $\Delta^{13}$C(‰) value at 15 min after the administration was 28.06±19.01 in the chronic pancreatitis rats, whereas the value was 51.27±3.21 in the normal rats; the value was significantly smaller in the chronic pancreatitis rats ($p<0.05$). (See FIG. 13.)

Figure 14:
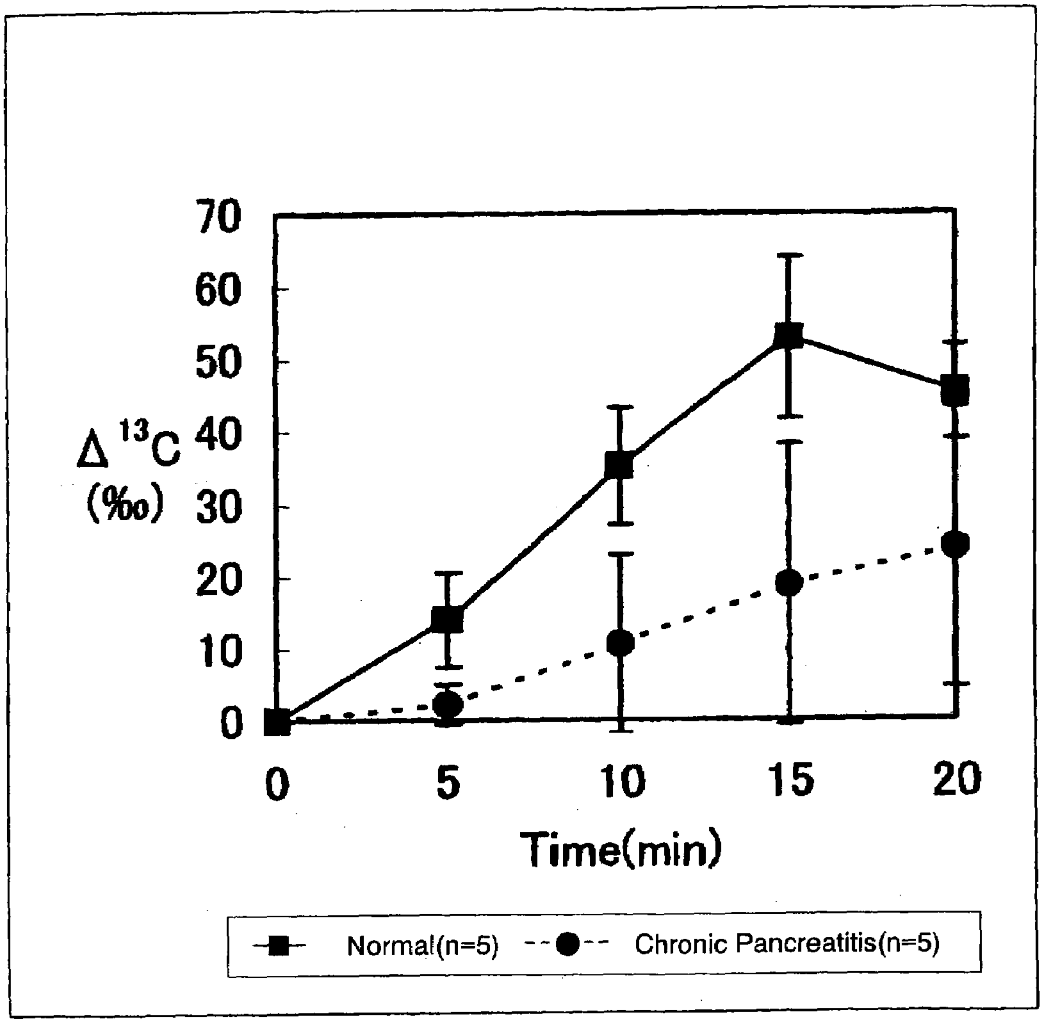
FIG. 14 shows the time course of the degree of increase of $^{13}C$ concentration in exhaled $CO_2$ ($\Delta^{13}C$(‰)) after administration of Bz-Val-($^{13}C$-Ala)-ONa. At 0 min, Bz-Val-($^{13}C$-Ala)-ONa was administered orally to chronic pancreatitis rats (●, n=5) and normal rats (■, n=5) at 11.0 mg/kg. The error bars represent SD.

The results of Bz-Val-($^{13}$C-Ala)-ONa breath test were as follows. The $\Delta^{13}$C(‰) value at 5 min after the administration was 2.21±2.74 in the chronic pancreatitis rats, whereas the value was 13.98±6.59 in the normal rats; the value was significantly smaller in the chronic pancreatitis rats ($p<0.01$). The $\Delta^{13}$C(‰) value at 10 min after the administration was 10.62±12.40 in the chronic pancreatitis rats, whereas the value was 35.22±8.02 in the normal rats; the value was significantly smaller in the chronic pancreatitis rats ($p<0.01$). The $\Delta^{13}$C(‰) value at 15 min after the administration was 18.80±19.39 in the chronic pancreatitis rats, whereas the value was 52.89±11.18 in the normal rats; the value was significantly smaller in the chronic pancreatitis rats ($p<0.01$). The $\Delta^{13}$C(‰) value at 20 min after the administration was 23.95±19.38 in the chronic pancreatitis rats, whereas the value was 45.38±6.53 in the normal rats; the value was significantly smaller in the chronic pancreatitis rats ($p<0.05$). (See FIG. 14.)

Figure 15:
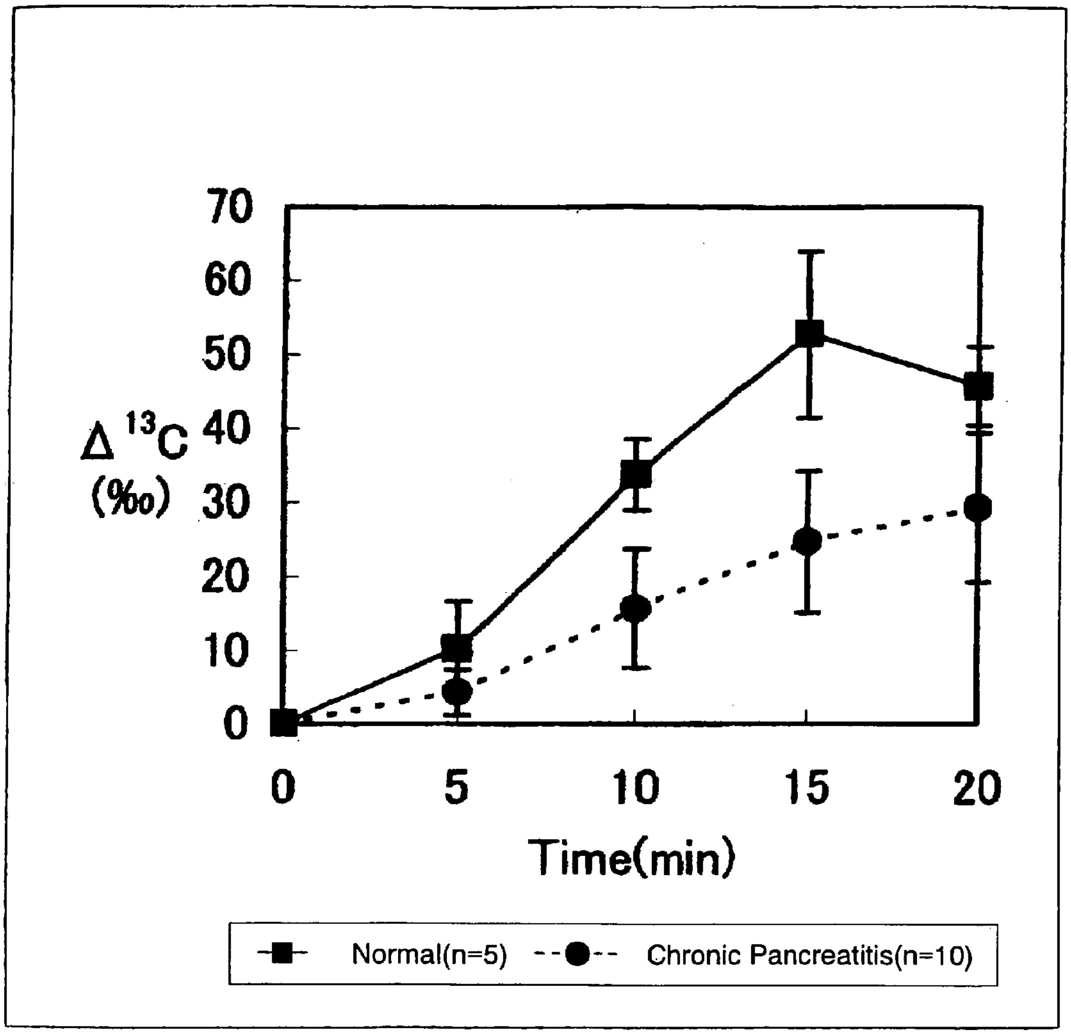
FIG. 15 shows the time course of the degree of increase of $^{13}C$ concentration in exhaled $CO_2$ ($\Delta^{13}C$(‰)) after administration of Bz-Tyr-($^{13}C$-Ala)-ONa. At 0 min, Bz-Tyr-($^{13}C$-

The results of Bz-Tyr-($^{13}$C-Ala)-ONa breath test were as follows. The $\Delta^{13}$C(‰) value at 5 min after the administration was 4.35±3.11 in the chronic pancreatitis rats, whereas the value was 10.33±6.34 in the normal rats; the value was significantly smaller in the chronic pancreatitis rats ($p<0.05$). The $\Delta^{13}$C(‰) value at 10 min after the administration was 15.65±7.93 in the chronic pancreatitis rats, whereas the value was 33.62±4.76 in the normal rats; the value was very significantly smaller in the chronic pancreatitis rats ($p<0.001$). The $\Delta^{13}$C(‰) value at 15 min after the administration was 24.68±9.48 in the chronic pancreatitis rats, whereas the value was 52.64±11.32 in the normal rats; the value was very significantly smaller in the chronic pancreatitis rats ($p<0.001$). The $\Delta^{13}$C(‰) value at 20 min after the administration was 29.25±9.98 in the chronic pancreatitis rats, whereas the value was 45.61±5.27 in the normal rats; the value was significantly smaller in the chronic pancreatitis rats ($p<0.01$). (See FIG. 15.)

The results of Bz-Met-($^{13}$C-Ala)-ONa breath test were as follows. The $\Delta^{13}$C(‰) value at 5 min after the administration was 1.52±1.47 in the chronic pancreatitis rats, whereas the value was 19.76±10.16 in the normal rats; the value was significantly smaller in the chronic pancreatitis rats ($p<0.01$). The $\Delta^{13}$C(‰) value at 10 min after the administration was 7.69±5.15 in the chronic pancreatitis rats, whereas the value was 48.88±17.45 in the normal rats; the value was very significantly smaller in the chronic pancreatitis rats ($p<0.001$). The $\Delta^{13}$C(‰) value at 15 min after the administration was 14.59±8.50 in the chronic pancreatitis rats, whereas the value was 45.53±8.00 in the normal rats; the value was very significantly smaller in the chronic pancreatitis rats ($p<0.0001$). The $\Delta^{13}$C(‰) value at 20 min after the administration was 20.25±9.43 in the chronic pancreatitis rats, whereas the value was 38.58±3.79 in the normal rats; the value was very significantly smaller in the chronic pancreatitis rats ($p<0.001$). (See FIG. 16.)

The results of Bz-Ser-($^{13}$C-Ala)-ONa breath test were as follows. The $\Delta^{13}C$(‰) value at 5 min after the administration was 1.07±1.43 in the chronic pancreatitis rats, whereas the value was 8.29±4.94 in the normal rats; the value was significantly smaller in the chronic pancreatitis rats ($p<0.05$). The $\Delta^{13}C$(‰) value at 10 min after the administration was 5.94±8.13 in the chronic pancreatitis rats, whereas the value was 35.91±11.85 in the normal rats; the value was significantly smaller in the chronic pancreatitis rats ($p<0.01$). The $\Delta^{13}C$(‰) value at 15 min after the administration was 10.34±11.99 in the chronic pancreatitis rats, whereas the value was 47.48±12.89 in the normal rats; the value was significantly smaller in the chronic pancreatitis rats ($p<0.01$). The $\Delta^{13}C$(‰) value at 20 min after the administration was 12.80±11.97 in the chronic pancreatitis rats, whereas the value was 43.04±5.30 in the normal rats; the value was very significantly smaller in the chronic pancreatitis rats ($p<0.001$). (See FIG. 17.)

The results of Bz-Thr-($^{13}$C-Ala)-ONa breath test were as follows. The $\Delta^{13}C$(‰) value at 10 min after the administration was 12.67±19.74 in the chronic pancreatitis rats, whereas the value was 47.36±10.99 in the normal rats; the value was significantly smaller in the chronic pancreatitis rats ($p<0.05$). The $\Delta^{13}C$(‰) value at 15 min after the administration was 19.78±24.70 in the chronic pancreatitis rats, whereas the value was 47.11±5.67 in the normal rats; the value was significantly smaller in the chronic pancreatitis rats ($p<0.05$). (See FIG. 18.)

The results of Boc-Phe-($^{13}$C-Ala)-ONa breath test were as follows. The $\Delta^{13}C$(‰) value at 5 min after the administration was 0.74±0.54 in the chronic pancreatitis rats, whereas the value was 5.02±3.79 in the normal rats; the value was significantly smaller in the chronic pancreatitis rats ($p<0.05$). The $\Delta^{13}C$(‰) value at 10 min after the administration was 3.43±1.46 in the chronic pancreatitis rats, whereas the value was 24.36±7.52 in the normal rats; the value was very significantly smaller in the chronic pancreatitis rats ($p<0.001$). The $\Delta^{13}C$(‰) value at 15 min after the administration was 6.36±2.67 in the chronic pancreatitis rats, whereas the value was 28.13±4.43 in the normal rats; the value was very significantly smaller in the chronic pancreatitis rats ($p<0.0001$). The $\Delta^{13}C$(‰) value at 20 min after the administration was 10.16±3.95 in the chronic pancreatitis rats, whereas the value was 25.09±2.00 in the normal rats; the value was very significantly smaller in the chronic pancreatitis rats ($p<0.0001$). (See FIG. 19.)

By a breath test with Bz-Phe-($^{13}$C-Ala)-ONa, Bz-Gln-($^{13}$C-Ala)-ONa, Bz-Val-($^{13}$C-Ala)-ONa, Bz-Tyr-($^{13}$C-Ala)-ONa, Bz-Met-($^{13}$C-Ala)-ONa, Bz-Ser-($^{13}$C-Ala)-ONa, Bz-Thr-($^{13}$C-Ala)-ONa or Boc-Phe-($^{13}$C-Ala)-ONa, it is possible to detect decreases in pancreatic exocrine function.

FORMULATION EXAMPLE 1

Internal Liquid Preparation

Purified water was added to 5 parts by weight of Bz-Phe-($^{13}$C-Ala)-Na to make a total of 100 parts by weight. After dissolution, the solution was sterilized with a filter. The filtrate was transferred into vials and sealed to make an internal liquid preparation.

All publications, patents and patent applications cited herein are incorporated herein by reference in their entity.

INDUSTRIAL APPLICABILITY

With the diagnostic agent for pancreatic exocrine function of the invention, a pancreatic exocrine function test has become possible in which the dose for one test can be reduced compared to $^{13}$C-peptides used in conventional test methods, without decreasing the degree of increase of $^{13}$C concentration in exhaled $CO_2$ ($\Delta^{13}C$ (‰)).

The diagnostic agent for pancreatic exocrine function of the invention may be used for pancreatitis screening tests in mass examinations or on persons hospitalized for through physical checkup. Further, the diagnostic agent of the invention may also be used for judgment of the severity of chronic pancreatitis, for prognostication of the worsening of fulminant hepatitis that still has a high mortality (30%), for diagnosis of the causative factors of pancreatitis, and for early diagnosis of pancreatic cancer. The diagnostic agent of the invention is also useful in making a diagnosis that denies pancreatitis in medical examination of general outpatients.

The invention claimed is:

1. A dipeptide represented by the following formula (I):

$$X_1—R_1—Y_1 \quad (I)$$

or a pharmaceutically acceptable salt thereof, wherein $X_1$ is a protecting group selected from the group consisting of benzoyl, acetyl, benzyloxycarbonyl and t-butyloxycarbonyl, $R_1$ is a glutamine, valine, tyrosine, methionine, serine or theronine residue, and $Y_1$ is a $^{13}$C-labeled alanine molecule optionally having a protecting group.

2. The dipeptide of claim 1, which is selected from the group consisting of the following compounds:

(a) Bz-Gln-($^{13}$C-Ala), (b) Bz-Val-($^{13}$C-Ala), (c) Bz-Tyr-($^{13}$C-Ala), (d) Bz-Met-($^{13}$C-Ala), (e) Bz-Ser-($^{13}$C-Ala), (f) Bz-Thr-($^{13}$C-Ala), (g) Ac-Met-($^{13}$C-Ala), (h) Z-Met-($^{13}$C-Ala), and (i) Boc-Met-($^{13}$C-Ala), wherein Bz is benzoyl, Ac is acetyl, Z is benzyloxycarbonyl, and Boc is t-butyloxycarbonyl.

3. A diagnostic agent for pancreatic exocrine function comprising a dipeptide represented by the following formula (I):

$$X_1—R_1—Y_1 \quad (I)$$

or a pharmaceutically acceptable salt thereof, wherein $X_1$ is a protecting group selected from the group consisting of benzoyl, acetyl, benzyloxycarbonyl and t-butyloxycarbonyl, $R_1$ is a glutamine, valine, tyrosine, methionine, serine or theronine residue, and $Y_1$ is a $^{13}$C-labeled alanine molecule optionally having a protecting group.

4. The diagnostic agent of claim 3, wherein the dipeptide represented by formula (I) is selected from the group consisting of the following compounds:

(a) Bz-Gln-($^{13}$C-Ala), (b) Bz-Val-($^{13}$C-Ala), (c) Bz-Tyr-($^{13}$ C-Ala), (d) Bz-Met-($^{13}$C-Ala), (e) Bz-Ser-($^{13}$C-Ala), (f) Bz-Thr-($^{13}$C-Ala), (g) Ac-Met-($^{13}$ C-Ala), (h) Z-Met-($^{13}$C-Ala), and (i) Boc-Met-($^{13}$C-Ala), wherein Bz is benzoyl, Ac is acetyl, Z is benzyloxycarbonyl, and Boc is t-butyloxycarbonyl.

* * * * *

UNITED STATES PATENT AND TRADEMARK OFFICE

CERTIFICATE OF CORRECTION

PATENT NO. : 7,208,525 B2
APPLICATION NO. : 10/482571
DATED : April 24, 2007
INVENTOR(S) : Tadashi Kohno et al.

It is certified that error appears in the above-identified patent and that said Letters Patent is hereby corrected as shown below:

On the Title Page, Item (57), in the Abstract, line 8, “Y1” should read --$Y_1$--.

In claim 1, column 24, line 23, “theronine” should read --threonine--.

In claim 3, column 24, line 48, “theronine” should read --threonine--.

In claim 4, column 24, line 56, “(c) Bz-Tyr-($^{13}$ C-Ala),” should read --(c) Bz-Tyr-($^{13}$C-Ala),--.

In claim 4, column 24, line 61, “(g) Ac-Met-($^{13}$ C-Ala),” should read --(g) Ac-Met-($^{13}$C-Ala),--.

Signed and Sealed this

Fourteenth Day of October, 2008

JON W. DUDAS
*Director of the United States Patent and Trademark Office*